(12) United States Patent
Quintanar et al.

(10) Patent No.: US 9,795,316 B2
(45) Date of Patent: Oct. 24, 2017

(54) RADIOLUCENT ELECTRODE OR SENSOR ASSEMBLY

(71) Applicant: LifeSync Corporation, Fort Lauderdale, FL (US)

(72) Inventors: Felix Quintanar, Boca Raton, FL (US); Kal Hendry, Coconut Creek, FL (US); Tom Nguyen, Coconut Creek, FL (US); Andrew Muser, Coral Springs, FL (US)

( * ) Notice: Subject to any disclaimer, the term of this patent is extended or adjusted under 35 U.S.C. 154(b) by 0 days.

(21) Appl. No.: 14/968,395

(22) Filed: Dec. 14, 2015

(65) Prior Publication Data

US 2016/0166170 A1    Jun. 16, 2016

Related U.S. Application Data

(63) Continuation of application No. 13/888,107, filed on May 6, 2013, now Pat. No. 9,211,075, which is a
(Continued)

(51) Int. Cl.
*A61B 5/04* (2006.01)
*A61B 5/0428* (2006.01)
(Continued)

(52) U.S. Cl.
CPC ........ *A61B 5/04286* (2013.01); *A61B 5/0408* (2013.01); *A61B 5/0424* (2013.01); *A61B 5/0478* (2013.01); *A61B 5/04085* (2013.01); *A61B 5/04087* (2013.01); *A61B 5/6822* (2013.01); *A61B 5/6823* (2013.01);
(Continued)

(58) Field of Classification Search
CPC .............. A61B 5/0408; A61B 5/04085; A61B 2562/164; A61B 5/0024; A61B 5/6833; A61B 2562/222; A61B 5/0402; A61N 1/0492; A61N 1/04; A61N 1/0476; A61N 1/36014; A61N 1/3718; A61N 2001/086
USPC ........ 600/372, 382, 384–386, 388–389, 391, 600/393; 607/129, 142
See application file for complete search history.

(56) References Cited

U.S. PATENT DOCUMENTS 4,353,372 A * 10/1982 Ayer .................. A61B 5/04085
174/117 FF
4,938,231 A * 7/1990 Milijasevic .......... A61N 1/0587
607/129

(Continued)

*Primary Examiner* — Joseph Stoklosa
*Assistant Examiner* — Brian M Antiskay
(74) *Attorney, Agent, or Firm* — Patzik, Frank & Samotny Ltd.

(57) ABSTRACT

A lightweight, disposable and substantially radiolucent electrode or sensor assembly for that universally connects to separate, non-integrated electrodes or sensors for the monitoring of the physiological parameters of a live subject wherein the electrode assembly is comprised of one or more radiolucent electrical connectors for connecting the electrode assembly to the sensors. The present invention also discloses a method of positioning the electrode assembly on a patient whose physiological signs are being monitored such that access to the patient's chest is substantially unimpeded so as not to obstruct the electromagnetic imaging of the patient's chest, the application of defibrillation paddles or surgical procedures that require access to the chest area.

30 Claims, 13 Drawing Sheets

Related U.S. Application Data continuation of application No. 12/020,156, filed on Jan. 25, 2008, now abandoned.

(60) Provisional application No. 60/897,390, filed on Jan. 25, 2007.

(51) Int. Cl.
*A61B 5/0408* (2006.01)
*A61B 5/0424* (2006.01)
*A61B 5/0478* (2006.01)
*A61B 5/00* (2006.01)
*A61N 1/00* (2006.01)

(52) U.S. Cl.
CPC . *A61B 2560/045* (2013.01); *A61B 2562/0209* (2013.01); *A61B 2562/0285* (2013.01); *A61B 2562/164* (2013.01); *A61B 2562/222* (2013.01); *A61B 2562/226* (2013.01); *A61B 2562/227* (2013.01)

(56) References Cited

U.S. PATENT DOCUMENTS

| | | | | |
|---|---|---|---|---|
| 5,191,886 A | * | 3/1993 | Paeth | A61B 5/04085 600/382 |
| 5,824,033 A | * | 10/1998 | Ferrari | A61B 5/04087 607/142 |
| 6,434,410 B1 | * | 8/2002 | Cordero | A61B 5/04085 600/391 |
| 2005/0251004 A1 | * | 11/2005 | Istvan | A61B 5/0006 600/395 |

\* cited by examiner

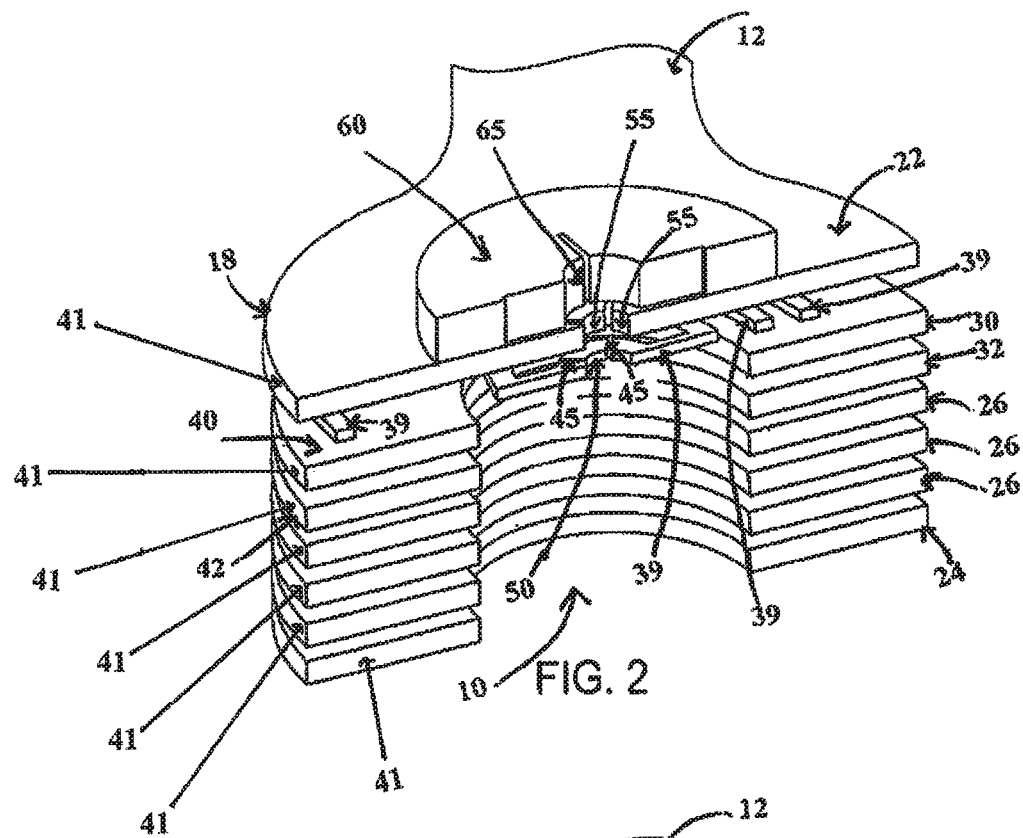
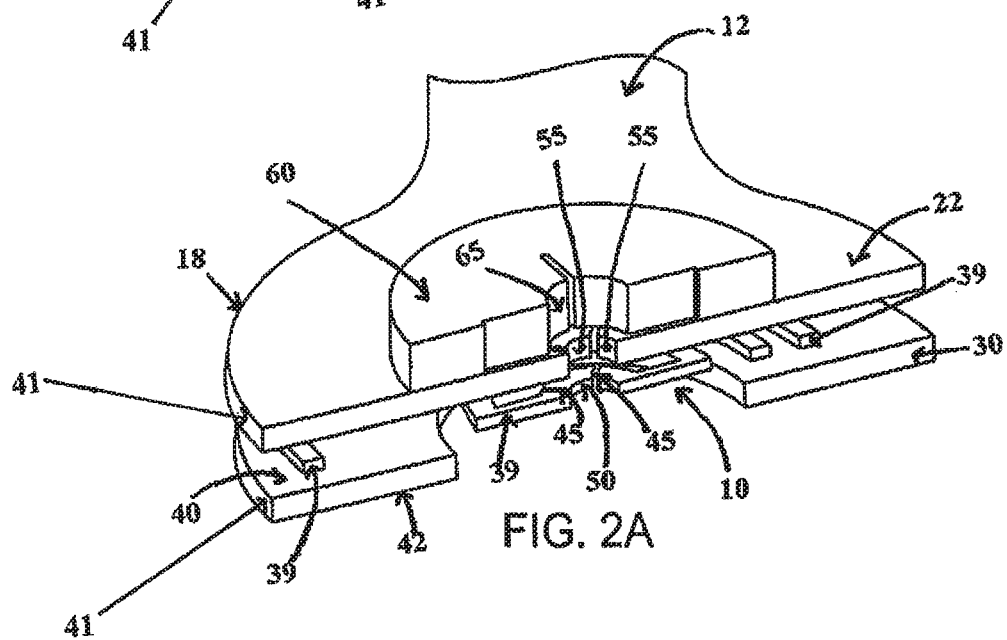

RADIOLUCENT ELECTRODE OR SENSOR ASSEMBLY

PRIORITY CLAIM

This application claims priority to U.S. patent application Ser. No. 13/888,107, filed on May 6, 2013, now issued U.S. Pat. No. 9,211,075, which corresponds to U.S. patent application Ser. No. 12/020,156, filed on Jan. 25, 2008, which corresponds to U.S. Provisional Application No. 60/897,390, filed on Jan. 25, 2007, which incorporates by reference U.S. patent application Ser. No. 09/998,733, filed on Nov. 30, 2001, now issued as U.S. Pat. No. 7,197,357, U.S. patent application Ser. No. 10/439,356, filed on May 16, 2003, U.S. patent application Ser. No. 11/077,934, filed on Mar. 11, 2005, U.S. patent application Ser. No. 11/105,230, filed on Apr. 12, 2005, U.S. patent application Ser. No. 11/105,231, filed on Apr. 12, 2005, U.S. patent application Ser. No. 11/105,232, filed on Apr. 12, 2005, and U.S. patent application Ser. No. 09/908,509, filed on Jul. 17, 2001, now issued as U.S. Pat. No. 6,611,705, the disclosure and contents of which are expressly incorporated herein by reference.

FIELD OF INVENTION

The present invention relates to a radiolucent lead wire replacement assembly for the monitoring of physiological data and to architectures having improved radiolucency for connecting flat printed circuits to sensors.

BACKGROUND OF THE INVENTION

The ability to monitor the physiological parameters of a live subject, and in particular a human patient, is crucial in determining the health status of the patient and the proper medical treatment to be applied to the patient, as well as in understanding the effects of certain variables on physiological processes while conducting research. Several physiological parameters, such as heart rate and brain wave activity, can be monitored by taking advantage of the fact that these processes involve the conduction of electricity within the body and therefore, produce detectable bio-signals. Measurement of these electrical signals has long been accomplished by applying electrically conductive sensors to the surface of the patient's skin or other tissues or by the invasive implantation of the sensor inside the patient's body. Typically, these detected or sensed electrical signals are then relayed to a separate monitoring device whereby the signals are processed and displayed in a useful form.

For example, an electrocardiograph (ECG) system monitors the electrical heart activity of a patient. Conventional ECG systems utilize electrodes or sensors which are placed on a patient's chest in specific locations to detect the electrical impulses generated by the heart during each beat. Usually, these electrical impulses or signals are directly transferred from each electrode or sensor to a nearby, stationary ECG monitor through individual lead wires or cables that are connected to each electrode or sensor. The ECG monitor performs various signal processing and computational operations to convert the raw electrical signals into meaningful information to be displayed or printed out for review by a physician. These systems generally require that the patient be tethered to a stationary monitor and remain sufficiently still in order that the electrodes and wire attachments are not disturbed. Restriction of the patient's movement is oftentimes cumbersome and uncomfortable for a patient and the attending medical staff. It is also ill-suited for emergency situations during which a patient's body must be rapidly moved to a variety of positions and transported to several locations.

In order to alleviate discomfort and to increase a patient's mobility, several portable telemetry systems exist for the monitoring of physiological parameters. Generally, two types of telemetry systems exist for the monitoring of ECG signals. One type of system requires placing conventional ECG electrodes on the skin surface of a patient and connecting the electrodes to a portable, patient-worn telemetry unit by one or more lead wires or cables. The telemetry unit wirelessly transmits the ECG signals to a remote monitoring device. Although the patient has greater mobility, there still exist some disadvantages. Because each electrode or sensor is individually connected to the telemetry unit by an individual lead wire or cable, the several lead wires or cables become confusingly intertwined making it difficult to make the proper corresponding connections between the electrodes and the telemetry unit. Also, because each electrode or sensor is placed separately on the patient, one at a time in a sequence, the chances of acquiring an inaccurate signal due to improper placement on the patient are high. Additionally, the motion of the individual current carrying lead wires in relation to each other causes the generation of electrical artifacts in the transmitted signal.

In order to solve these problems associated with individual electrodes or sensors and their corresponding lead wires, the second type of wireless telemetry system eliminates all wires extending from the electrodes and replaces them with a self-contained strip or patch-like assembly which incorporates the electrodes and the lead wires. The strip or patch assembly is then adhered to the patient's skin or otherwise worn on the body. Generally, the assembly is comprised of a thin and flexible substrate constructed of non-conducting material with the electrodes or conductive areas intended to be in contact with the patient and fully integrated into the surface of the substrate that is in contact with the skin. As such, the electrodes or conductive areas are fixed in set positions thereby greatly reducing the possibility of placing one or more of them improperly on the patient. One or more transmitters or transceivers and the corresponding circuitry are also integrated into the assembly's surface for wirelessly transmitting the detected ECG signals to a remote monitoring location. However, these types of fully-integrated electrode assemblies have several disadvantages stemming from their high cost and lack of flexibility in permitting alternative placement of the electrodes.

For example, most conventional ECG electrodes are relatively inexpensive and detachable from the lead wires so that they may be easily disposed of after each use in case of a failure or defect in the electrode and to maintain a relatively sterile environment that is necessary for medical use. With respect to fully-integrated electrode assemblies, in order to dispose of a failed electrode or sensor element, the entire assembly must impractically be discarded. Also, the entire assembly, if not disposable, must be meticulously cleaned after each use or each patient. Furthermore, most electrodes require the application of aqueous silver chloride gel or hydrogel to the surface of the electrodes to increase their conductivity. These gels will rapidly dry out and lose their conductivity. In order to preserve these gels after being pre-applied to the electrodes, the electrodes must be hermetically sealed when packaged. Thus, when the gels are applied to fully-integrated electrode assemblies, the entire assembly must be hermetically sealed for storage. Once opened, the assembly has no shelf life and must be used immediately or discarded.

Several disadvantages also stem from the use of fully-integrated electrode assemblies. For example, because the electrode or conductive surfaces are generally fixed in one position, the electrode assembly cannot be adapted to varying body sizes. Because of this lack of adaptability, applications that require placing the electrodes at un-conventional positions on the body would require manufacturing several separate configurations of the assembly. Also, because the electrode assembly is fully self-contained, the patient must uncomfortably bear the weight of the entire system, including the telemetry circuitry, on the chest. For neonatal and elderly patients, who tend to be relatively weak, have lower body weight, and generally thinner skin or more sensitive skin than do patients of other ages, this can be very uncomfortable. Furthermore, the power source (e.g. batteries), telemetry circuitry or other electronics may generate external heat that can add to the discomfort or potentially burn or irritate a patient's skin.

To combat the high cost and discomfort associated with a fully-integrated electrode assembly while still maintaining the advantages of an easy to place sensor assembly, disposable chest assemblies that contain a plurality of fixed connections for connecting to separate, conventional electrodes or sensors have been developed. Typically, such chest assemblies consist of a thin and flexible substrate constructed of non-conductive material that spans across the length of the chest. Printed onto or embedded within the substrate are conductive traces that run along its surface extending from the electrode connections to one or more common terminals or trunks. The terminal or trunk connects to a separate monitoring device such as a patient-worn telemetry unit that is attached to a more comfortable weight-bearing location on the body than the chest or is wired to a bedside monitor. Despite these efforts, a long-standing unmet need still exists for a chest assembly of the foregoing type that may be universally connected to a conventional electrode or sensor without significant physical hardship on the patient.

Because the shape and size of conventional electrodes or sensors are not standardized, they are not universally compatible with many of the wires, leads or chest assemblies used in physiological data collection systems. To solve this problem, many wired systems utilize spring-loaded, female-type snap pieces that can adapt to differently-shaped male snap pieces or metal tabs of the electrodes or sensors. These spring-loaded pieces are relatively expensive and cannot be amortized over the life of a disposable chest assembly. Also, because it is important that any fastener fit tightly to the electrode or sensor in order to avoid a conductivity gap, the amount of pressure needed to snap the pieces together can be physically difficult.

With the increasing use of electromagnetic diagnostic imaging devices, including but not limited to x-rays, fluoroscopes, CAT scans and magnetic resonance imaging, there is a further need for lead wires and electrode assemblies that are transparent to these imaging devices. The devices need to be configured and constructed to be sufficiently radiolucent and radiotransparent for medical treatment applications. Conventional wired and wireless ECG systems, particularly those with chest-worn components, significantly interfere with the normal use and viewing of an X-ray film, fluoroscopic or other image that is created by electromagnetic radiation. Due to the desirability of using good conductors, such as metals, in the chest-worn electrodes, sensors and other components to provide a good electrical path for the sensor, these components are oftentimes substantially not radiolucent or radiotransparent and appear as blemishes or shadows at or worse, are completely opaque on the diagnostic image. For an attending physician, it is highly advantageous to be able to monitor an ECG or other vital signs which serve as an indication of a patient's physiological stability while simultaneously viewing the patient's internal organs (e.g. view of the internal blood vessels during cardiac catheterization or angiography); especially during emergency medical procedures in which time is of the essence. Also, because the chest assemblies typically span the entire chest, they greatly impair access for surgical procedures and usually need to be removed during surgery and other medical treatments that require unimpeded access to the chest area.

Efforts have been made to improve the translucency or permeability to X-ray of the electrodes or sensors themselves by lessening the mass or density of the metallic parts used in their construction. For example, a thin layer of metallic foil or conductive paint or ink has been used on the conductive surfaces of heart monitoring and stimulating electrodes. However, to compensate for the decreased thickness of the metallic conductive cross-section, the overall surface area of the foil or painted area must be increased to provide the same amount of conductivity. Because the electrodes or sensors are normally being applied to the non-flat surface of a 3-dimensional object, they often need to be placed at an angle to the viewing plane of the diagnostic device. When placed at these angles, even very thin and flat metallic areas that span a wide surface area appear much thicker on an X-ray film or other image. Also, thin foils or paints which may provide the desired degree of radiolucency are more fragile than solid metallic parts and are more easily worn down or chipped from abrasion.

In another example, the metallic components of an electrode or sensor have been completely eliminated and replaced with one or more layers of thin, carbon or graphite-filled polymers, often in conjunction with conductive adhesives or gels. Lead wires that connect to the electrodes have also been substituted with cables of insulated, carbon fibers. However, these polymers are generally composed of very thin, carbon filaments or particles thereby having the characteristic of high impedance such that a large amount of external heat is generated by a flowing current. As such, carbon based conductors alone will rarely withstand an external defibrillation current applied to the body. To prevent destruction of the conductor due to exposure to higher than normal electrical currents, a thin coating of silver/silver chloride is applied to the surface of the carbon material. Unfortunately the application of the silver/silver chloride negatively affects the electrode's radiolucency and may make it opaque. Furthermore, while carbon or graphite may be more radiolucent than a comparably sized metallic conductor, carbon or graphite materials are less conductive than metals and therefore require a greater quantity of carbon or graphite to conduct the same amount of electricity as a metal counterpart. Thus, the carbon or graphite-filled polymers or cables are relatively thick in comparison making them relatively unwieldy when worn by a patient. Further, the increased thickness of the materials reduces the radiolucency and shows up unsatisfactorily on the resulting images. This is particularly problematic with depth-capturing images such as computed tomography (CT) scans.

Efforts have been made to provide radiolucent current spreading layers within defibrillation or heart-stimulating electrodes. In one example, a conductive mesh backing made of low-resistance, non-corrosive and pliable metal wires is applied to a skin-contacting conductive polymer adhesive matrix or pad such that the open space of the mesh is greater than about 50%. In another example, a pattern of metal or otherwise conductive ink is applied to the surface of a conductive polymer sheet. The objective of the mesh or ink patterns is to provide enough conductive surface so that there is a low amount of electrical resistance for the conduction of high voltage defibrillation pulses without burning or generating a lot of heat, and remaining somewhat radiolucent. Thus, the amount of conductive surface required in these applications is substantially more than is required in an electrode that is simply used for monitoring. Neither of these applications addresses a radiolucent connection to an electrode or sensor that is electrically suitable for the initial acquisition of an electrical signal. Rather, they are only concerned with spreading a large amount of applied current on the backend of the circuit path along the skin surface.

Therefore, it is an object of the present invention to provide a lightweight, disposable and substantially radiolucent chest assembly that universally connects to separate, non-integrated electrodes or sensors for use in a wireless system for monitoring the physiological parameters of a live subject.

SUMMARY OF THE INVENTION

The present invention relates to a radiolucent ECG electrode assembly that can be made universally compatible with existing or conventional ECG monitors and electrodes. However, it is not intended that the invention be limited to an ECG system as it has utility in any system that acquires physiological parameters from a patient using sensors and allows for the monitoring of physiological data. In a preferred embodiment, the ECG system generally comprises a lightweight, portable, radiolucent or radiotransparent chest assembly and a body electronics unit containing the electronic components required to acquire a signal from the electrodes and transmit the same wirelessly, and a base station for receiving the wireless signal. For purposes of this disclosure, "radiolucent" is defined as being wholly or partially permeable to radiation so as to be translucent, transparent or nearly invisible in an X-ray so as not to unduly interfere with the appearance of or unacceptably impair the ability to detect physical abnormalities of an X-rayed subject by the normal use and viewing of an X-ray film. The chest assembly connects to separate electrodes which are intended to be placed at specific locations on the patient's body for detecting the electrical signals of the patient's heart; providing up to a "7-lead" analysis of the heart. Alternatively, the chest assembly can be augmented with a precordial assembly that connects to electrodes specifically located on the patient's body, thus providing a "12-lead" analysis of the heart.

The electrical signals are transmitted through the chest assembly and/or the precordial assembly to any conventional ECG monitor (including any legacy ECG monitor) by way of an adapter. In a preferred embodiment, the electrical signals are transmitted wirelessly and the chest assembly and/or precordial assembly are connected to a body electronics unit, which is removably secured to the patient. For example, the body electronics unit may be attached to the patient's arm using a releasable arm band. The body electronics unit transmits the electrical signals to the base station via radio transmission and may utilize two-way wireless communication protocols which are generally known in the art (e.g. BLUETOOTH® or WiFi®). Therefore, the wires that ordinarily tether a patient to an ECG monitor are conveniently replaced by a radio link. The base station contains terminals configured to attach to standard lead wires or cables and transmits the electrical signals to a conventional ECG monitor through these standard lead wires or cables. The ECG monitor then processes or transforms the electrical signals into meaningful information that can be reviewed or otherwise used by a physician.

In addition to collecting and transmitting ECG signals, the present invention is capable of collecting and transmitting other physiological data. For example, the body electronics unit is capable of transmitting and the base station is capable of receiving and processing physiological data pertaining to a patient's pulse, respiration rate, heart rate, temperature, blood pressure, EEG signals, and pulse oximeter signals, or the like.

In particular, the present invention provides a radiolucent or radiotransparent chest assembly comprising a flexible circuit with electrically conductive elements or traces that run along a base layer of polyester film (e.g. MYLAR®) or other lightweight, flexible and non-conductive material that is of sufficient thickness so as to not to be damaged when bent. The chest assembly also contains a plurality of radiolucent or radiotransparent connectors in fixed positions that connect to any conventional electrode or sensor by way of an electrode connector. The connectors are configured such that an electrical connection is made between each electrode or sensor and a conductive element or trace of the chest assembly. The conductive elements or traces terminate at a common trunk at which point a terminal connector mechanically and electrically connects the chest assembly to the body electronics unit. This connector may include a mechanism for producing an alert when there is an improper connection to the separate body electronics unit or other monitor. In general, the chest assembly is to be comprised of substantially radiolucent or radiotransparent materials.

The electrically conductive elements or traces of the chest assembly may be of silver epoxy ink or any other suitable conductive material (e.g. copper, gold, carbon, carbon nanotube, indium tin oxide, and graphite, generally in an epoxy base) that is embossed, printed or otherwise permanently applied to the substrate in any other suitable fashion known in the art. The conductive elements or traces generally run substantially side-by-side one another, in a substantially linear fashion and separated by sufficient distance such that electrical arcing or "cross-talk" among the conductive elements or traces is substantially avoided. As a result, electrical artifacts are also substantially reduced thereby greatly improving the quality of the signals being monitored. The width and/or thickness of the conductive elements or traces and the distance required between them may be varied depending upon the conductive properties of the conductive material used for the conductive elements or traces. By using materials that are highly conductive for the elements or traces, very thin elements or traces may be applied to the substrate thereby increasing the radiolucency or radiotransparency of the chest assembly. Therefore, the advantage is that different conductive materials can be used in the same electrode connector or assembly to achieve the desired degree of conductivity, radiolucency and cost. One or more insulating layers are applied over the electrically conductive elements to protect the integrity of the signals. Also, one or more shielding layers constructed of dielectric material, or other suitable material, may be applied to either side of the base layer in order to reduce distortion of the signals from external interference including radio frequency noise. Lastly, the chest assembly may have one or more outer layers constructed of lightweight and reasonably moisture-resistant material (e.g. DuPont SONTARA®) or other suitable fabric and may be laser or die cut in order to avoid sharp edges along the chest assembly. Preferably, the chest assembly is constructed of the thinnest and least number of layers electrically possible in order to reduce the weight and the density of the assembly to improve its comfort and radiolucency.

The configuration of the plurality of fixed electrode or sensor connectors of the chest assembly provides several advantages. For example, because the connectors are fixed in a set position within the chest assembly and connect to a series of permanently fixed, streamlined conductive elements or traces, the assembly is very simplistic and there is little possibility of improperly placing the chest assembly on the patient as it is designed to fall easily into place. Another advantage when the connectors separately connect to any conventional electrode or sensor by way of the electrode housing described below, is that the chest assembly may be removed from the patient, repositioned or interchanged with another assembly without ripping the electrode adhesives off of the patient each time such a change is desired. Similarly, bad electrodes can be replaced without having to discard the entire assembly.

The electrode connector comprises an aperture therethrough for receiving an electrode or sensor and may be formed from any cut pattern that will universally, tightly grip a variety of sized and shaped conductors on electrodes or sensors that are designed to protrude through the aperture. Examples of suitable geometries for the aperture include forming the aperture by a straight, oval, crescent, cross or triangular-shaped cut. Preferably, the aperture is formed from a star cut pattern that is die cut, punched, laser cut or formed by other known means. The star cut pattern defines flaps that mechanically hold the electrode or sensor in the aperture. The flaps are also electrically conductive and are contiguous to the electrically conductive element of the chest assembly and provide an electrical connection between the electrically conductive element or trace and the electrode or sensor upon insertion of the electrode or sensor in the aperture. The use of more than one cross cut through the material allow the flaps to better conform to the conductor inserted in the aperture and therefore permits a more stable electrical contact patch. In operation, the male portion of the electrode or sensor is inserted through the aperture starting at the patient side of the chest assembly. The flaps formed by the aperture are deflected as the male portion of the electrode or sensor is inserted into the aperture. The resilience of the flaps cause the flaps to wipe against the male portion and mechanically grip the electrode or sensor tightly within the aperture defined between the flaps. The electrode or sensor is inserted into the aperture until the contact portion of the electrode or sensor (such as a male snap post) abuts or contacts the electrically conductive element of the flaps.

In addition, the present invention relates to an electrode housing for fastening the electrode or sensor connectors of the chest assembly to a conventional electrode. Preferably, such a housing has a terminal configured for connecting to the male portion of an electrode having a snap terminal. The electrode housing, secured to the non-skin contacting side of the chest assembly, is constructed of a radiolucent, elastomeric material fastened to the back surface of the chest assembly and contains a female void, aligned with the aperture of the electrode or sensor connector, for receiving and removably securing a male portion of the electrode or sensor. Preferably, the female void is slightly undersized to assure a tight mechanical fit on the male portion of the electrode or sensor. The elastomeric or resiliency property of the electrode housing allows the female void to receive and secure electrodes or sensors having different shapes and sizes. At each connection point, the chest assembly may optionally include an electrically conductive, adhesive layer for removably securing the electrode or sensor to the chest assembly and providing enhanced electrical connection between the electrically conductive element or trace and the electrode or sensor upon insertion of the electrode or sensor through the aperture of the connector and electrode housing.

The electrode connectors of the present invention differ from those known in the art in that they are constructed to be highly radiolucent by eliminating a large amount of the non-radiolucent conductive surface area surrounding the connection. Yet, the connectors retain sufficient conductive surface area to provide a robust and reliable electrical connection to a separate electrode or sensor and still have the ability to withstand defibrillation shocks to the body.

Devices known in the art use a circular disk or otherwise solid areas composed of conductive materials (particularly metals), which are deposited around the aperture at the point of connection to the electrode. However, these solid areas are relatively impermeable to X-rays and therefore are highly visible on the resulting images. Accordingly, the present invention provides a radiolucent electrode or sensor connector whereby one or more of the conductive elements, traces or lead wires of the chest assembly seamlessly extends all the way to the aperture of the connector and forms various geometries that provide a continuous electrical path from the chest assembly to the sensor, but leaves much of the typical, substrate area of the flaps free of solid conductive area by being largely comprised of non-conductive elements. Preferably, the conductive element or trace terminates into a single, small dot of sufficient size to encircle the aperture.

It will be readily apparent to one of skill in the art upon reading this document that a variety of geometries may be used so long as the connector region remains substantially radiolucent, even when turned at an angle to the viewing plane. The electrical contact patch between the conductor on the flap and the sensor must be of sufficient size to conduct the low level currents from the sensor without undue voltage loss at the monitoring end. While this can be as limited as simply terminating the conductive trace on a single flap, such connection may not be electrically robust enough for use in a critical care setting. Alternative embodiments which would provide greater redundancy of the electrical connection between the flaps and the sensor may be required. In one embodiment, the conductive trace terminates into two concentric, thin conductive circles that surround the aperture. The innermost circle is broken by the cuts used to create the flaps. The concentric circles are interconnected with a plurality of axial connections between the inner and outer circle. In a most preferred embodiment, there are four flaps, with each flap having an axial connection between the circles. It is likely that configurations of two or three flaps will provide sufficient current carrying ability. One of skill in the art will readily recognize that the current carrying capacity of any individual axial connection can be reduced when there are multiple axial connections. This allows for the use of thinner traces when constructing axial leads. It is readily apparent to one of skill in the art that the circles can be any geometric shape which can surround the aperture. Neither the outer or inner circle must be continuous. This invention contemplates the use of conductive surfaces which do not fully encircle the electrode. This is possible when the electrode itself has a 360° degree electrical contact patch. In such instance the use of semi-circles or other partial geometries are possible so long as the total contact area with the electrode is robust enough to provide an acceptable signal and where necessary, can withstand a defibrillation shock without self-destructing. These and other variations and modifications in the invention will be apparent to those skilled in the art without departing from the scope of the invention.

As such, one object of the present invention is to meet the long-felt need for a radiolucent electrode or sensor assembly. Another advantage of the present invention is that by creating a seamless and continuous electrical path around the electrode or sensor, the acquired signals are for more robust than signals which are acquired by directly anchoring or attaching a lead wire to the electrode. Also, the common occurrence of hot spots generated by electron build-up at abrupt connections between an electrode and a lead wire is eliminated. By eliminating hot spots, the clarity of the signals acquired from the electrode or sensor is greatly improved and the chances of having an interrupted vital signal are reduced. Also, there is far less chance of a patient being burned by the electronics and the assembly.

The chest assembly of the present invention further improves the radiolucency of these types of monitoring devices by offering the option to route part of the assembly outside of the area to be imaged. Typically, the chest assembly is placed on the chest such that the assembly lies across the chest and spans the entire chest width and/or length. However, the chest assembly of the present invention is not limited to a particular shape or configuration as the chest assembly is formed with expandable arms or extensions, each terminating at an electrode or sensor connector in order to connect to electrodes or sensors at variable positions and in far reach along the body. The arms are cut in a serpentine, or other expandable pattern, and are preferably constructed of polypropylene or polyethylene fabric, KAPTON®, MYLAR®, or other flexible, memoryless material. The ability to relocate a sensor in some instances allows for removing the sensor and chest assembly from the area to be imaged by routing the assembly out of the imaged area.

Furthermore, the present invention also discloses a method for further removing from the chest area that portion of the chest assembly which crosses horizontally across the chest by placing or slinging the chest assembly around the back of the neck with the electrode connectors still maintaining proper placement along conventional ECG positions around the periphery of the chest. Thus, the chest assembly is configured to be of sufficient length for use around the neck and the electrode connectors are configured so as to line the periphery of the chest without crossing the chest area. By placing the chest assembly over the neck, the comfort to the patient may be increased as a portion of the assembly is no longer lying on the chest wall. Also, the chest area is left substantially free such that surgery, imaging procedures, and other medical treatments occupying the chest area may be accomplished while still monitoring the patient's ECG.

While the ability to flexibly place individual electrodes allows the electrodes to be positioned out of the field of view, the inventors hereof have discovered that the electrode connector for the conventional ground or reference ECG electrode that is typically associated with the right leg is sometimes improperly positioned by the user such that it crosses the abdomen and unnecessarily imposes on the body areas that are being imaged. As the placement of this electrode is not deemed to be critical, the present embodiment fixes this electrode in a location which is unlikely to show up in the imaging.

These as well as other novel advantages, details, embodiments, features, and objects of the present invention will be apparent to those skilled in the art from the following detailed description of the invention, the attached claims and accompanying drawings, listed herein below which are useful in explaining the invention.

BRIEF DESCRIPTION OF THE DRAWINGS

FIG. 2 is an exploded cross sectional view of a preferred embodiment of the electrode assembly.

FIG. 2A is an exploded cross sectional view of an alternative embodiment of the electrode assembly.

FIG. 12A depicts an x-ray film of a patient's chest in which the electrode assembly of the present invention was applied to the patient's chest.

DETAILED DESCRIPTION OF THE INVENTION

For a better understanding of the present invention, reference may be had to the following detailed description taken in conjunction with the appended claims and the accompanying drawings.

Figure 1:
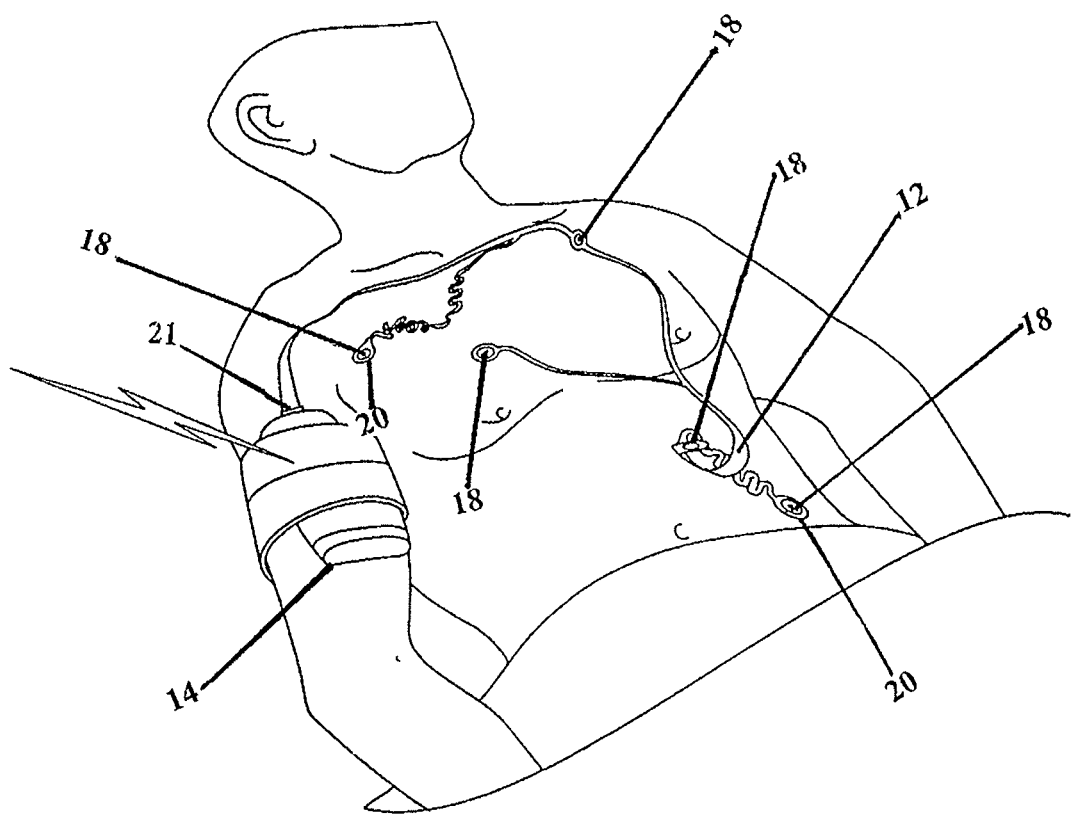
FIG. 1 is a perspective view of an exemplary embodiment of the electrode assembly as being used in a wireless electrocardiograph system.

Referring to FIG. 1, the chest assembly 12 is preferably a one-piece flexible circuit that connects a plurality of electrode connectors 18 whereby the electrode connectors 18 are configured to connect to electrodes 20 or electrically conductive adhesives. Preferably, the electrode connectors 18 have snap terminals that connect to electrodes 20 having snap terminals. As shown in detail in FIG. 3, each electrode connector 18 connects to an electrically conductive element or trace 39 for transmitting electrical signals. The electrically conductive elements or traces 39 run along the chest assembly 12 and connect to a chest assembly connector 21.

Alternatively, the chest assembly 12 may be constructed with electrode conductors, instead of electrode connectors. In such an embodiment, each electrode conductor will have a flat, conductive surface. Electrodes having flat conductive surfaces may be coupled to the electrode conductors via a suitable conductive adhesive. Thus, electrodes can be attached to the chest assembly by "sticking" an electrode to each electrode conductor.

Figure 3:
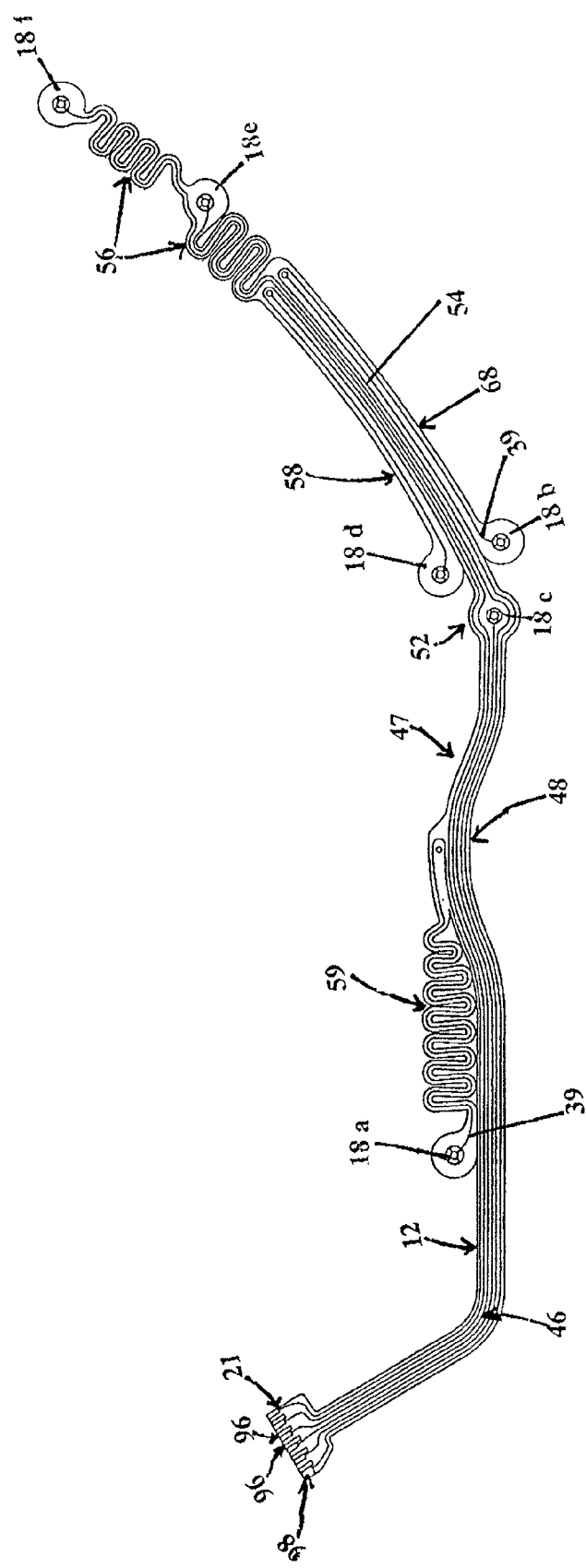
FIG. 3 is a top view of an exemplary embodiment of the electrode assembly in the form of a chest assembly whereby the skin-contacting surface of the assembly is being shown.

FIG. 2 depicts a cross section of the chest assembly 12 at one of the electrode connector portions 18. As shown in FIG. 2, the chest assembly 12 may have one or more outer layers 22, 24 that are comprised of any lightweight, flexible, moisture resistant, radiolucent or radiotransparent, and non-conductive material that is of sufficient thickness so as to not to be damaged when bent. For example, the outer layers may be made of DuPont SONTARA®, polyethylene terephthalate (PET) or a liquid crystal polymer (LCP). The outer layers 22, 24 may be laser or die cut in order to avoid sharp edges along the chest assembly 12. The chest assembly 12 may be constructed with only one outer layer or no outer layers without departing from the spirit and scope of the invention. Moreover, if the chest assembly is constructed with just one outer layer, that outer layer can be on either side of the chest assembly 12 without departing from the spirit and scope of the invention. One or more adhesive layers 26 may be used to secure the outer layers 22, 24 to one or more insulating or dielectric layers 30, 32. Insulating or dielectric layers 30, 32 may be constructed of MYLAR® (polyester) film or other suitable insulating material, such as Paralyne C. Layers 30, 32 have a first side 40 and a second side 42. The electrically conductive elements or traces 39 that connect to the electrode connectors 18 may be located on the first side 40 of layer 30. The electrically conductive elements or traces of the chest assembly may be of silver epoxy ink or any other suitable conductive material (e.g. copper, gold, carbon, carbon nanotube, indium tin oxide, and graphite, generally in an epoxy base) that is embossed, printed or otherwise permanently applied to the substrate 41 in any other suitable fashion known in the art. As shown in FIGS. 2 and 3, the conductive elements or traces 39 run substantially side-by-side one another, in a fixed relationship and separated by sufficient distance such that electrical arcing or "cross-talk" among the conductive elements or traces is substantially avoided. During construction of the chest assembly, the width and/or thickness of the conductive elements or traces 39 and the respective distance between them may be varied depending upon the conductive properties of the conductive material chosen for the conductive elements or traces.

By using materials that are highly conductive for the elements or traces 39, very thin elements or traces may be applied to the substrate 41 thereby increasing the radiolucency or radiotransparency of the chest assembly 12. It is appreciated that one of ordinary skill in the art could determine the optimum width of the conductive elements or traces and the separation between the elements or traces by taking into consideration the physical parameters of the materials being used for the elements and the layers of the electrode assembly, the foreseeable operating conditions in which the electrode assembly will be used, and the manufacturing capabilities. Adequate current-carrying capacity, reducing the occurrence of electrical arcing, radiolucency and radiotransparency are some of the considerations that should be made in determining the dimensions of the conductive elements or traces. Furthermore, the ability of the electrode assembly to maintain electrical and physical integrity during and after defibrillation is an extremely important consideration that must be undertaken when determining the dimensions of the conductive elements or traces and the dielectric layers. In order to meet the requirements of the current ANSI standard for defibrillation withstand, the electrode assembly must be able to survive a minimum of a 5000V discharge into the patient, during application of either a monoplasic or biplasic defibrillation waveform, whereby the energy delivered to the assembly is 360 joules. Preferably, the chest assembly 12 is constructed of the thinnest and least number of layers electrically possible in order to reduce the weight and the density of the assembly to improve its comfort and radiolucency. For example, in the alternative embodiment shown in FIG. 2A, the chest assembly 12 may be constructed to have a minimum configuration of only three layers. The three layers could consist of just a single dielectric or insulating layer 30, the layer of electrically conductive elements or traces 39, and a single outer layer 22.

A shielding layer (not shown) for further reducing any external interferences or radio frequency noise with the chest assembly 12 may be located on the second side 42 of the dielectric or insulating layer 32. The shielding layer may be constructed of single or multiple layers of dielectric, or electrically or magnetically conductive material. Of course, the chest assembly 12 may be constructed without a shielding layer without departing from the spirit and scope of the invention. If applied, the shielding layer is preferably comprised of an X-patterned grid. The back of the electrode connector 18 may also be covered with Mylar® to further insulate the chest assembly 12 and prevent an externally applied electric potential from entering the ECG system.

The chest assembly 12 may also be constructed with an adhesive sheet (not shown) that partially or completely covers the chest assembly 12. The electrode connectors 18 may be sandwiched between the adhesive sheet and the outer layer 24 of the chest assembly 12. Alternatively, electrode conductors may be used instead of electrode connectors 18. Preferably, the adhesive sheet is constructed of polymers that have isotropic electrical conductive properties and/or anisotropic electrical conductive properties such that the regional specific impedance through the adhesive sheet is less than in a laterally oriented direction. The polymers are preferably hydropolymers, which are electrically conductive, relatively non-irritating to a patient's skin, and demonstrate excellent adhesive qualities. Suitable hydropolymer sheets for use with the present invention are available from Promeon of Boston, Mass., under the product designation RG-60 Series Hydrogels. In another exemplary embodiment, the adhesive having isotropic electrical conductive properties could be applied to the electrode connector 18 or the electrode conductor just prior to the attachment of the electrode 20 to the chest assembly 12. The adhesive could be applied between the electrode connector 18 or electrode conductor and the electrode 20 or to the side of the electrode 20 that contacts or connects to the patient. In such an embodiment, the chest assembly 12 would not be manufactured with an adhesive sheet. Instead, the health care provider would apply the adhesive to the electrode connector 18 or electrode conductor and/or electrode 20 just prior to attaching the chest assembly 12 to the patient.

The chest assembly 12 may be constructed to connect to any conventional electrode or sensor. More specifically, as shown in FIGS. 2 and 2A, at each point (i.e. connection point 10) where an electrode or sensor connects to the chest assembly 12, portions of the layers of the chest assembly 12 that reside on the patient side are removed or are not applied during manufacture and the first side 40 of the dielectric or insulating layer 30 containing the electrically conductive element or trace 39 is exposed. At each electrode or sensor connection point 10, the chest assembly 12 optionally includes an electrically conductive layer (not shown) that is adhered to the electrically conductive element or trace 39. The optional electrical adhesive layer may be a layer of silver epoxy or other suitable electrically conductive, adhesive material capable of adhering or securing the electrode or sensor to the chest assembly 12 and providing an electrical link between the electrode or sensor with the electrically conductive element or trace 39.

Figure 11:
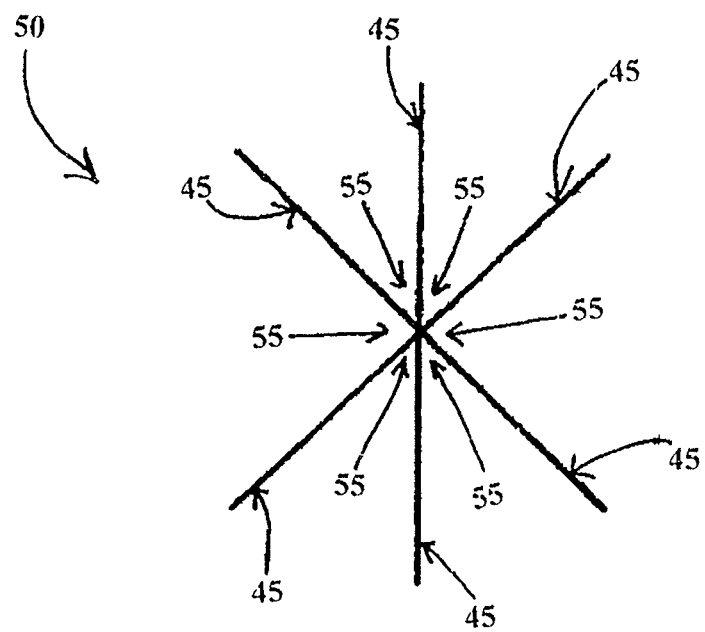
FIGS. 11A-E depict exemplary embodiments of an aperture formed in the electrode assembly at the site of the electrode connector for receiving an electrode.
Figure 11:
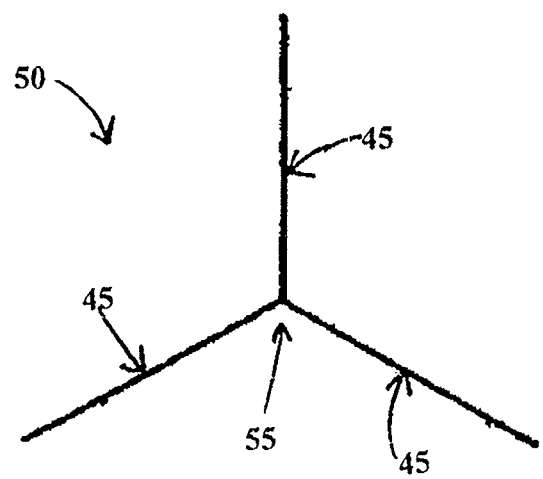
Figure 11:
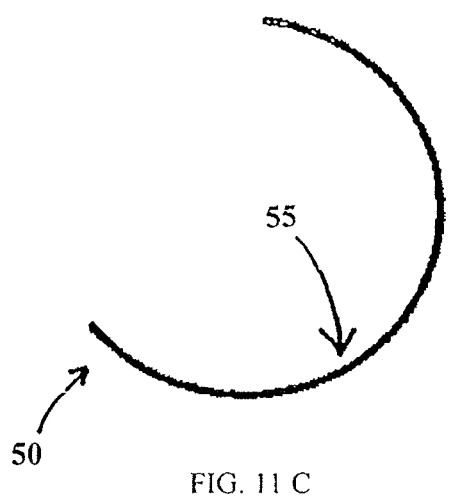
Figure 11:
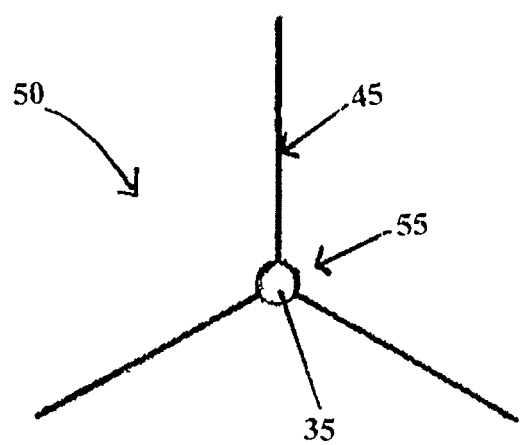
Figure 11:
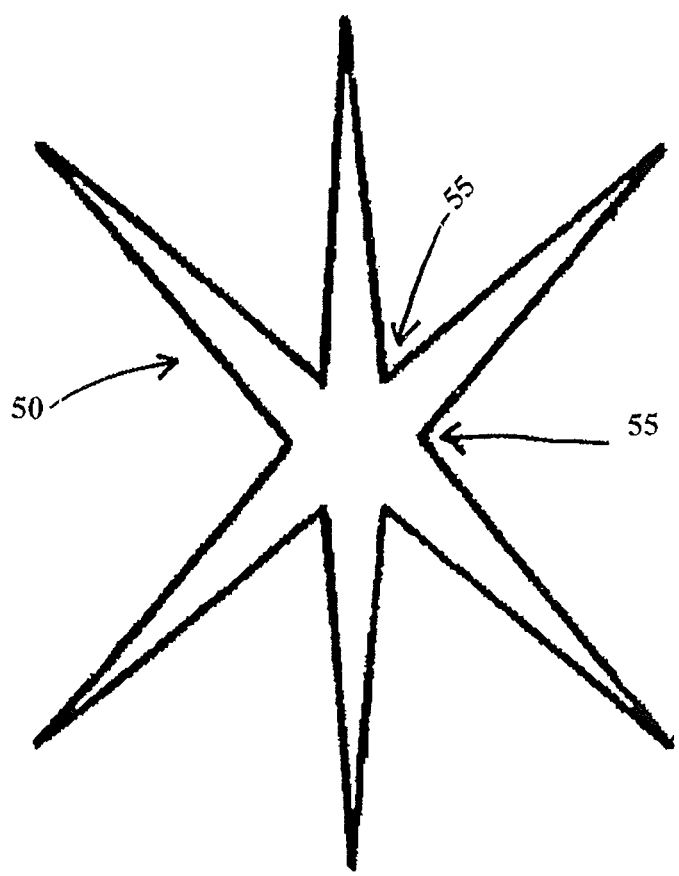

In addition, at each electrode or sensor connection point 10, the chest assembly 12 includes an aperture 50 formed therethrough. As shown in detail in FIG. 11A, the aperture 50 may be defined by a star cut pattern in the form of an asterisk with six legs 45 cut through each layer of the lead assembly 12. Flaps 55 are defined by the pairs of adjacent legs 45. The aperture 50 may be cut in various shapes and configurations without departing from the scope and spirit of the invention. For example, as shown in FIG. 11B, the aperture 50 formed may be defined by three flaps 55. Further, as shown in FIG. 11C, the aperture 50 may be defined by a semi-circular cut through the chest assembly 12, which forms one flap 55. In addition, as shown in FIG. 11D, the aperture 50 may be defined by three flaps 55 and an open passage 35 formed where the three flaps 55 contact each other. Moreover, as shown in FIG. 11E, the aperture 50 may be defined by a star cut pattern with spacing between adjacent flaps 55. The flaps 55 are also electrically conductive and are contiguous to the electrically conductive element 39 of the chest assembly and provide an electrical connection between the electrically conductive element or trace 39 and the electrode or sensor upon insertion of the electrode or sensor in the aperture.

Referring back to FIGS. 2 and 2A, at each electrode or sensor connection point 10, the chest assembly 12 includes an electrode housing 60 on the non-skin contacting side of the chest assembly 12. The electrode housing 60 may be constructed from an elastomeric rubber, or any other suitable elastomeric or plastic material. The electrode housing 60 may be thermally bonded to the chest assembly 12 or adhered to the chest assembly 12 with any suitable adhesive. The electrode housing 60 contains an appropriately sized female void 65 for receiving the male portion of any conventional electrode or sensor 20. The electrode housing 60 should be constructed from a suitable elastomeric material so that the female void 65 will conform to different male portions of different shapes and sizes when such male portions are inserted up through the aperture 50 and into the female void 65. Accordingly, upon insertion of the male portion, the female void 65 conforms such that the male portion is removably secured in the female void 65. Because of the aforementioned design and configuration of the chest assembly, the chest assembly can be used with many different electrodes or sensors 20 that are used in the healthcare industry. In addition, to aid the health care provider in attaching the chest assembly 12 to the patient, each electrode housing 60 is preferably appropriately color coded and/or contains alphanumeric designations to correspond to the particular electrode or sensor 20 attached to that electrode housing 60. For example, the electrode housing 60 may be labeled RL, LA, LL, RA or V when the chest assembly is intended for ECG use. In yet another embodiment, the electrode housing 60 is not bonded to the chest assembly 20, but is provided separately. In such an embodiment, the technician or health care provider setting up the equipment would press on the separate electrode housings 60 when attaching the chest assembly 12 to the electrode or sensor 20.

To connect a conventional electrode or sensor 20, the male portion of an electrode or sensor 20 is inserted into or positioned through the aperture 50. As the electrode or sensor 20 is inserted through the aperture 50, the male portion of the electrode or sensor 20 deflects the flaps 55. The resilience of the flaps 55 causes the flaps 55 to wipe against the male portion and mechanically hold the electrode or sensor 20 in the aperture 50 that is defined between the flaps 55. The pattern of the aperture 50 allows for the deflection of the flaps 55 with minimal force applied during the insertion of the male portion of the electrode or sensor 20. The male portion of the electrode or sensor 20 causes deflection of the flaps 55 without placing undue stresses on the ends of the flaps 55 which could otherwise result in the flaps being torn or losing their resilient property. In addition, because the aperture 50 is formed through the electrically conductive element or trace 39 (as shown in FIGS. 2-2A and 4-7), electrical conductivity is obtained when the electrode or sensor 20 contacts the flaps 55. Further, when the electrode or sensor 20 firmly abuts or contacts the electrically conductive elements or traces 39 via the flaps 55, the electrical signals corresponding to physiological data of the patient pass from the electrode or sensor 20 to the electrically conductive element or trace 39, which, in turn, conveys the data to the body electronics unit 14 (as shown in FIG. 1).

In another embodiment, the chest assembly 12 may be constructed such that a conductive male connector is used to connect a conventional electrode or sensor 20 that has a female receptacle or void instead of a male portion. To connect the conventional electrode or sensor 20 having the female receptacle or void, the conductive male connector is inserted through the aperture 50 until a first male member is removably secured in the electrode housing 60. The conductive male connector contacts the electrically conductive element or trace 39 upon insertion. The electrode or sensor 20 having the female receptacle or void is then removably connected to a second male member. Alternatively, the male conductive connector may be integrally connected or fixedly secured to the electrode housing 60. In such an embodiment, the electrode housing 60 would not be constructed of elastomeric material and would not contain the female void. In either case, the electrical signals corresponding to physiological data of the patient pass from the electrode or sensor 20 to the conductive male connector and to the electrically conductive element or trace 39.

Figure 4:
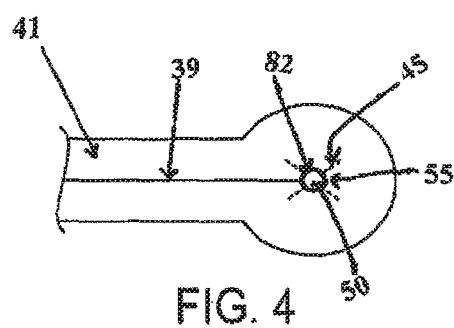
FIG. 4 is a top view of a preferred embodiment of the electrical connector of the electrode assembly.
Figure 6:
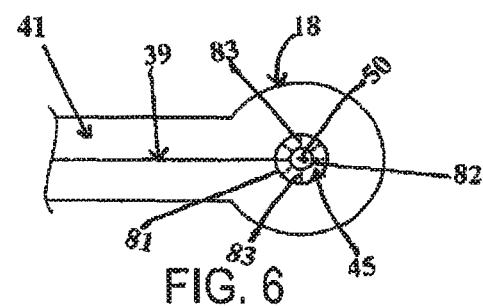
FIG. 6 is a top view of another preferred embodiment of the electrical connector of the electrode assembly.
Figure 5:
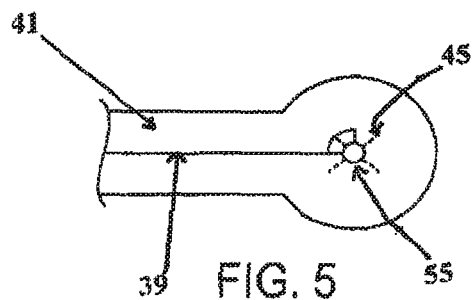
FIG. 5 is a top view of another exemplary embodiment of the electrical connector of the electrode assembly.

The electrode or sensor connector 18 is preferably constructed to be radiolucent or radiotransparent whereby one or more of the conductive elements, traces or lead wires 39 of the chest assembly 12 seamlessly extends all the way to the aperture 50 of the connector 18 and forms various geometries that provide a continuous electrical path from the conductive elements or traces 39 to the electrode or sensor 20, but leaves much of the typical, substrate 41 area of the flaps 55 free of solid conductive area by being largely comprised of non-conductive elements. As shown in FIG. 4, preferably, the conductive element or trace 39 terminates into a single, small dot 82 of sufficient size to encircle the aperture 50.

Figure 7:
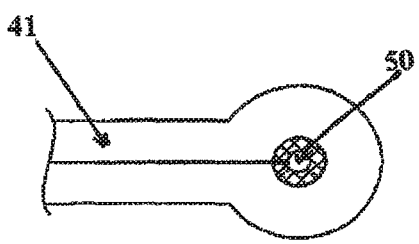
FIG. 7 is a top view of another exemplary embodiment of the electrical connector of the electrode assembly.

A variety of geometries may be used so long as the connector region remains substantially radiolucent, even when turned at an angle to the viewing plane. The electrical contact patch between the conductive area on the flap 55 and the electrode or sensor 20 must be of sufficient size to conduct the low level currents from the electrode or sensor 20 without undue voltage loss at the monitoring end. While this can be as limited as simply terminating the conductive trace 39 on a single flap 55, such a connection may not be electrically robust enough for use in a critical care setting. Alternative embodiments which would provide greater redundancy of the electrical connection between the flaps 55 and the electrode or sensor 20 may be required. For example, in one embodiment shown in FIG. 6, the conductive trace 39 terminates into two concentric, thin conductive circles 81 and 82 that surround the aperture 50. The innermost circle 82 is broken by the cuts 45 used to create the flaps 55. The concentric circles 81 and 82 are interconnected with a plurality of axial connections 83 between the inner and outer circles 81 and 82. In a most preferred embodiment shown in FIG. 6, there are four flaps 55, with each flap 55 having an axial connection 83 between the circles. It is likely that configurations of two or three flaps 55 will provide sufficient current carrying ability. One of skill in the art will readily recognize that the current carrying capacity of any individual axial connection 83 can be reduced when there are multiple axial connections. This allows for the use of thinner traces when constructing axial leads. It is also readily apparent to one of skill in the art that the circles 81 and 82 can be any geometric shape which can surround the aperture 50, such as those depicted in FIGS. 5 and 7. While the outer or inner circles 81 and 82 can be continuous circles, they do not need to be and may only partially encircle the aperture. In fact, it is preferable to have conductive surfaces which do not fully encircle the electrode in order to reduce the area of potential non radiolucent conductors. This is readily achievable when the electrode itself has a 360° degree electrical contact patch. In such instance the use of semi-circles or other partial geometries, such as a mesh configuration shown in FIG. 7, are possible so long as the total contact area with the electrode is robust enough to provide an acceptable signal and where necessary, can withstand a defibrillation shock without self-destructing. These and other variations and modifications in the invention will be apparent to those skilled in the art without departing from the scope of the invention.

Preferably, the chest assembly 12 and the electrodes or sensors used with the chest assembly are constructed of radiolucent or radiotransparent materials. Radiolucent electrodes are known in the art and are sold by companies such as Kendle and 3M. In addition, the chest assembly 12 is preferably designed and configured to be used only a few times before being disposed. Accordingly, the chest assembly 12 is preferably constructed such that the electrodes or sensors 20 can be connected to and disconnected from the chest assembly 12 only a limited amount of times before the connection between the chest assembly 12 and the electrodes or sensors 20 become unusable and the chest assembly must be discarded. For example, repeated use of the connection and disconnection of the electrodes or sensors 20 to and from the chest assembly 12 may cause the electrically conductive element or trace 39 to abrade or wear, the flaps 45 to lose their resiliency, or the elastomeric material defining the female void 65 to become overly stretched by the male portion of the electrode. A disposable chest assembly 12 has many advantages. For example, disposable chest assemblies using the present invention offer hygienic advantages since such chest assemblies will be disposed of after each patient use—thus, reducing the spread of infection and disease. Further, assemblies of the present design may be made radiolucent by selection of appropriate materials thereby enabling their use in medical procedures where traditional snaps would interfere with imaging equipment. Further, the materials used to construct a disposable chest assembly, which uses the present invention are significantly less expensive than the materials used on other known disposable systems. Thus, the structure and construction of the present invention makes a disposable chest assembly very cost effective compared to other known disposable systems.

Referring back to FIGS. 1 and 3, the chest assembly 12 is capable of attaching to five or six electrodes 20 and provides a means for generally positioning the electrodes on the patient, thereby providing up to a "7 lead" analysis of the electrical activity of the heart. The electrode connectors 18 are preferably labeled and color-coded to ensure that the chest assembly 12 is properly positioned on the patient and connected to the appropriate electrodes. For instance, the electrode connectors are preferably labeled RL, LA, LL, RA and V, respectively. The chest assembly 12 is constructed such that the RA electrode connector is connected to an electrode positioned on the right side of the patient's chest about level of the first and second intercostal space, the LA electrode connector is connected to an electrode positioned on the left side of the patient's chest about level of the first and second intercostal space, the RL and LL electrode connectors are connected to electrodes positioned on the left side of the patient's torso, and the V electrode connector is connected to an electrode positioned in the middle of the patient's chest about level of the fourth and fifth intercostal space. The chest assembly 12 is preferably designed such that it is centered on the chest below the patient's clavicle.

Referring to FIGS. 1 and 3, the chest assembly 12 is configured to provide flexible positioning of the chest assembly 12 on the patient. FIGS. 1 and 3 are for illustrative purposes only, and thus, the chest assembly 12, as depicted in FIGS. 1 and 3, is not limited to any particular shape or configuration. FIG. 3 depicts the chest assembly 12 as having six electrode connectors 18. The chest assembly 12 has a linear section or tail 46 extending from the chest assembly connector 21. The tail 46 flows into an electrode retaining section 47. The electrode retaining section 47 has an arcuate section 48. The RA electrode connector 18a attaches to the first expandable arm 59. The arcuate section 48 flows into a transition section 52. The transition section 52 flows into a linear run 54. The LA electrode connector 18c attaches to the linear run 54. A second expandable arm 56, a first extension arm 58 and a second extension arm 68 attach to the linear run 54. The VA electrode connector 18d attaches to the first extension arm 58 and the VB electrode connector 18b attaches to the second extension arm 68. The RL electrode connector 18e and the LL electrode connector 18f attach to the second expandable arm 56. As mentioned above, the electrode connector for the conventional ground or reference ECG electrode that is typically associated with the right leg (i.e. the RL electrode connector labeled as 18e) is, in practice, sometimes improperly positioned by the user such that it crosses the abdomen and unnecessarily imposes on the body areas that are being imaged. As the placement of this electrode is not deemed to be critical, the present embodiment fixes this electrode in a location which is unlikely to show up in the imaging (as shown in a fixed position at expandable arm 56 in FIG. 3).

The expandable arms 56, 59 are die cut in a serpentine pattern. The expandable arms 56, 59 comprise polypropylene or polyethylene fabric, Kapton, MYLAR®, or other flexible, memoryless material. The expandable arms 56, 59 expand, if necessary, by elongating the serpentine pattern. When expanded, a portion or the entire expandable arm is extended. Where only a portion of the expandable arm is extended, another portion remains folded. The expandable arms 56, 59 allow for extension as needed so that the chest assembly 12 can fit patients of various sizes and also allow for patient movement when the patient is wearing the chest assembly 12. The one or more extension arms 58, 68 allow for flexible positioning of the V electrode connector in the middle of the patient's chest such as placement at the electrode position V1, V2 or V3. In some instances, the health care practitioner may desire not to utilize the extension arms 58, 68 for taking electrocardiograph measurements. Thus, the extension arms 58, 68 may be removably and/or selectively secured to the linear run 54 in order to ensure that the extension arms 58, 68 will not interfere with the placement and positioning of the chest assembly and to allow unimpeded access to the chest area. For example, the extension arms 58, 68 may be die cut with a perforated seam that connects the extension arms 58, 68 to the linear run 54 along the length of the extension arms 58, 68. If the health care practitioner desires to use the extension arms 58, 68, the perforated seam is left unbroken so that the extension arms 58, 68 can be selectively positioned on the patient's chest.

Figure 3A:
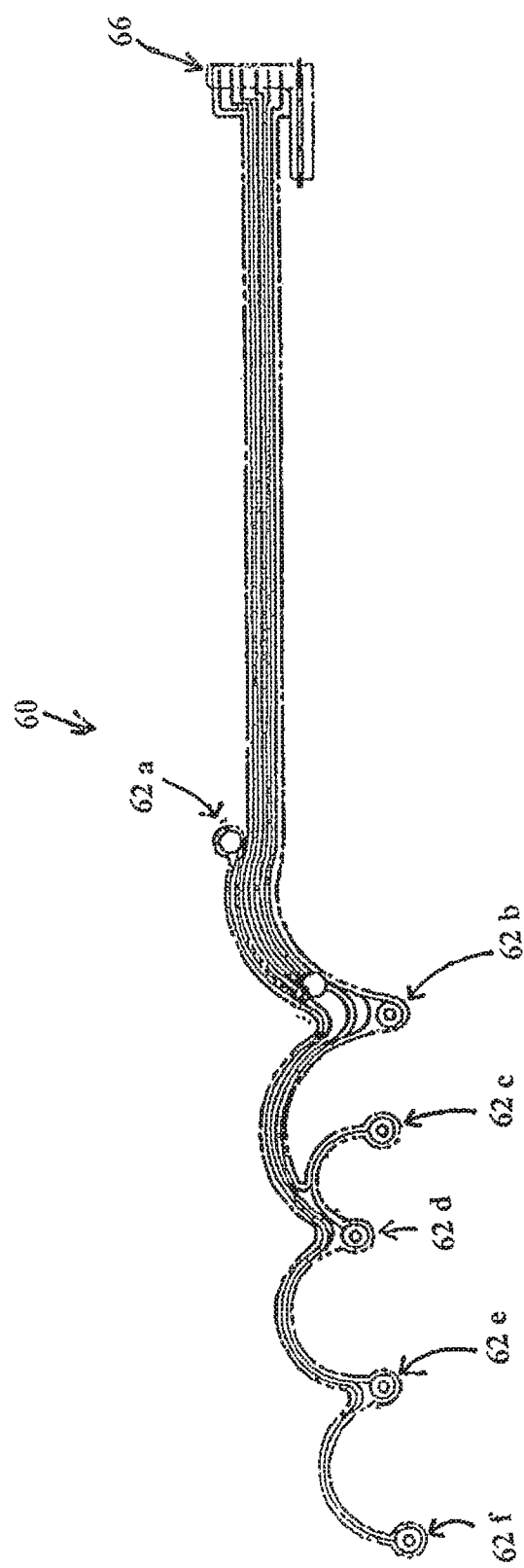
FIG. 3A is a top view of an exemplary embodiment of the electrode assembly in the form of a precordial assembly whereby the skin-contacting surface of the assembly is being shown.

Referring to FIG. 3A, the chest assembly 12 can be used with a precordial assembly 60 to provide a "12-lead" analysis of the electrical activity of the heart. Similar to the chest assembly 12, the precordial assembly 60 is a one-piece flexible circuit that connects a plurality of electrode connectors 62*a-f*. The electrode connectors 62 have snap terminals that connect to electrodes having snap terminals. Each electrode connector 62 connects to an electrically conductive element or trace for transmitting electrical signals from a patient's heart. The electrically conductive elements or traces run along the precordial assembly 60 and connect to a precordial assembly connector 66. The precordial assembly 60 may be constructed similarly to the chest assembly 12 discussed above.

The precordial assembly 60 is capable of attaching to six electrodes selectively positioned on the abdomen and the middle of the chest of the patient. The electrode connectors 62 of the precordial assembly 60 are preferably labeled and color-coded so as to prevent a health care provider from applying or positioning the precordial assembly onto the patient improperly. For instance, the electrode connectors 62 are preferably labeled V1, V2, V3, V4, V5 and V6, respectively. When the precordial assembly 60 is used, the V electrode connector on the chest assembly 12 is removed from its electrode and replaced with an electrode connector on the precordial assembly 60.

In operation, the chest assembly 12 and the precordial assembly 60 detect electrical signals generated by the heart during each beat and transfer these signals to the body electronics unit 14. When the system is operating in "7-lead" mode (i.e. when only the chest assembly 12 is being used), the body electronics unit 14 acquires signals from the RL, RA, LL, LA and V electrodes. The body electronics unit 14 uses the RL electrode as a ground reference. When the system is operating in the "12-lead" mode (i.e. the chest assembly 12 and the precordial assembly 60 are being used), the body electronics unit 14 acquires signals from the RL, RA, LL and LA electrodes via the chest assembly 12 and acquires signals from the V1, V2, V3, V4, V5 and V6 electrodes via the precordial assembly 60. Alternatively, a various number of electrodes may be monitored by the system. For example, the health care provider or physician may choose to use only two electrodes to monitor the heart, seven electrodes to monitor the heart, and so on. In other words, the present system is not limited to performing a "7-lead" and "12-lead" analysis of the heart. In addition, to detect the electrical signals from the heart, the chest assembly 12 and the precordial assembly 60 may be constructed to detect or transmit other vital signs of the patient which are detected by electrodes or sensors (e.g. pulse rate, respiration rate, heart rate and EEG).

Figure 8:
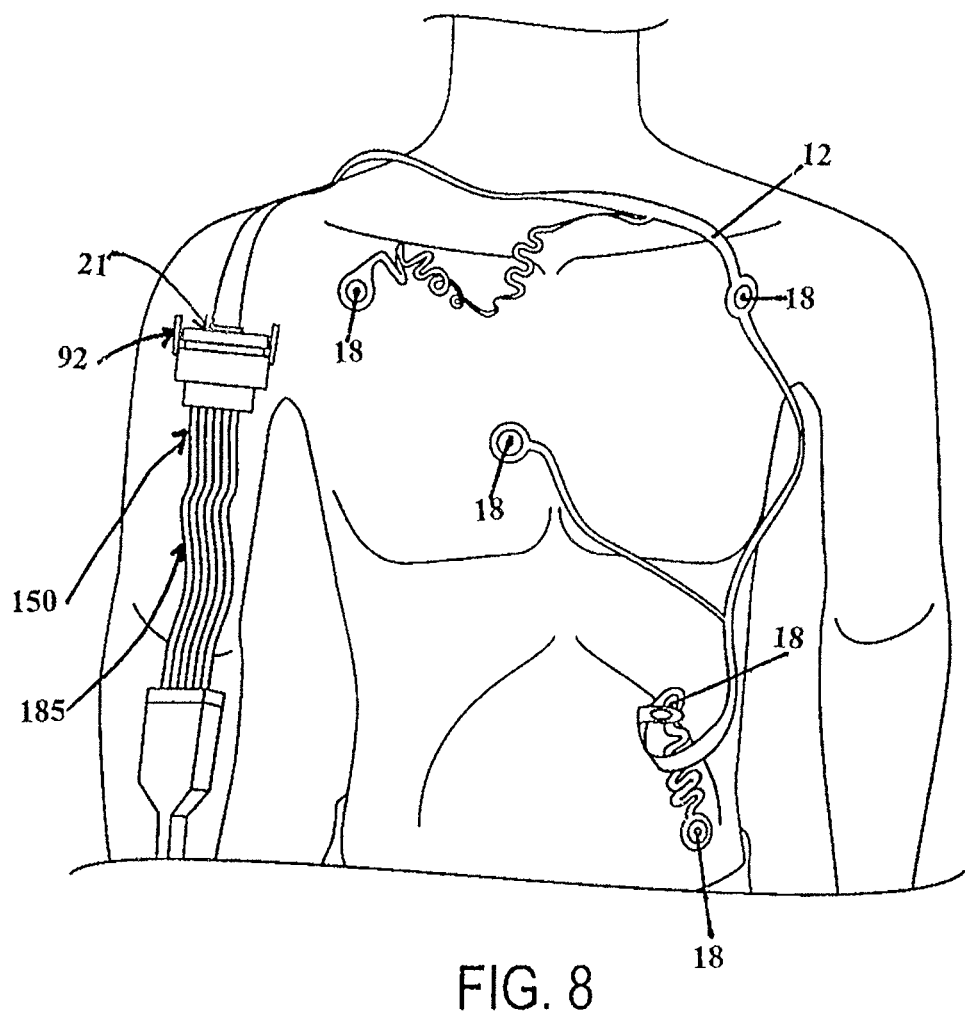
FIG. 8 depicts the placement of the electrode assembly around the outer periphery of a patient's torso.
Figure 9:
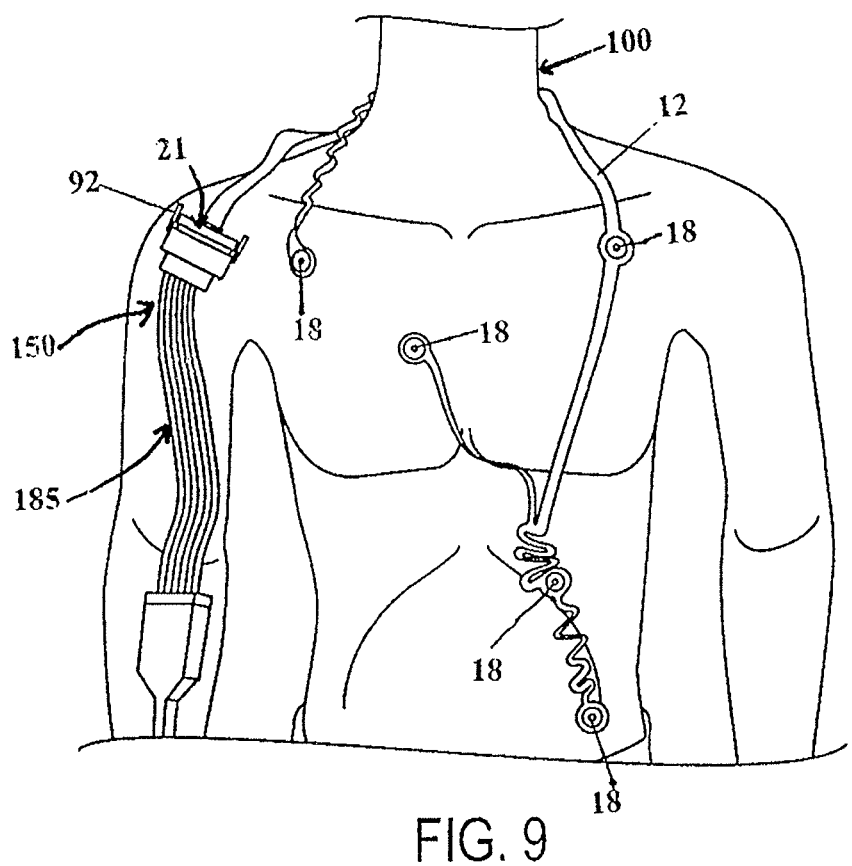
FIG. 9 depicts the placement of the electrode assembly whereby a portion of the electrode assembly is placed around the back of a patient's neck.

The chest assembly 12 of the present invention further improves the radiolucency of these types of monitoring devices by routing part of the assembly 12 outside of the area being imaged by electromagnetic diagnostic imaging devices such as X-ray, fluoroscopes, CAT scans and other magnetic resonance imaging devices. Typically, the chest assembly 12 is placed on the chest such that the assembly lies across the chest and spans the entire chest width and/or length as described above. In contrast, the present invention discloses a method, as shown in FIG. 8, in which the chest assembly 12 is of flexible size and configuration such that the electrode connectors 18 do not need to span horizontally across the chest. Rather, they may be applied around the periphery of the chest area while still maintaining proper placement along conventional ECG positions. As shown in FIG. 9, the present invention also discloses a method for removing from the chest area that portion of the chest assembly 12 which crosses horizontally across the chest by placing or slinging the chest assembly 12 around the back of the neck 100 with the electrode connectors 18 still maintaining proper placement along conventional ECG positions around the periphery of the chest. Thus, the chest assembly 12 is configured to be of sufficient length for use around the neck 100 and the electrode connectors 18 are configured so as to line the periphery of the chest without crossing the chest area. By placing the chest assembly 12 over the neck, the comfort to the patient is increased as a portion of the assembly is no longer lying on the chest wall. Also, the chest area is left substantially free such that surgery, imaging procedures, and other medical treatments occupying the chest area may be accomplished while still monitoring the patient's ECG.

Referring back to FIG. 1, the chest assembly 12 connects to the body electronics unit 14 via a chest assembly connector 21. Specifically, the chest assembly connector 21 inserts into a chest assembly port located in the body electronics unit 14. Similarly, the precordial assembly 60 (not shown in FIG. 1) connects to the body electronics unit 14 via the precordial assembly connector 66. Specifically, the precordial assembly connector 66 inserts into a precordial assembly port. Resistors are connected to the chest assembly port and the precordial assembly port to prevent excessive electrical current from entering the body electronics unit 14 thereby ensuring that the body electronics unit 14 continues to operate properly in the presence of a strong electrical current caused by a defibrillator (i.e. a 5 kV defibrillator excitation). The chest assembly connector 21 and the precordial assembly connector 66 are specifically keyed or configured to prevent the assembly connectors 21, 66 from being inserted into the assembly ports backwards, misaligned or otherwise improperly. Moreover, the chest assembly connector 21 is keyed or configured such that it is not compatible with the precordial assembly port. Likewise, the precordial assembly connector 66 is keyed or configured such that it is not compatible with the chest assembly port. For example, the chest assembly connector 21 and/or the precordial assembly connector 66 could have tongues specifically configured or arranged to fit into corresponding grooves of the chest assembly port and the precordial assembly port, respectively. Accordingly, the chest assembly connector 21 can only be connected to the chest assembly port in one orientation.

Figure 10:
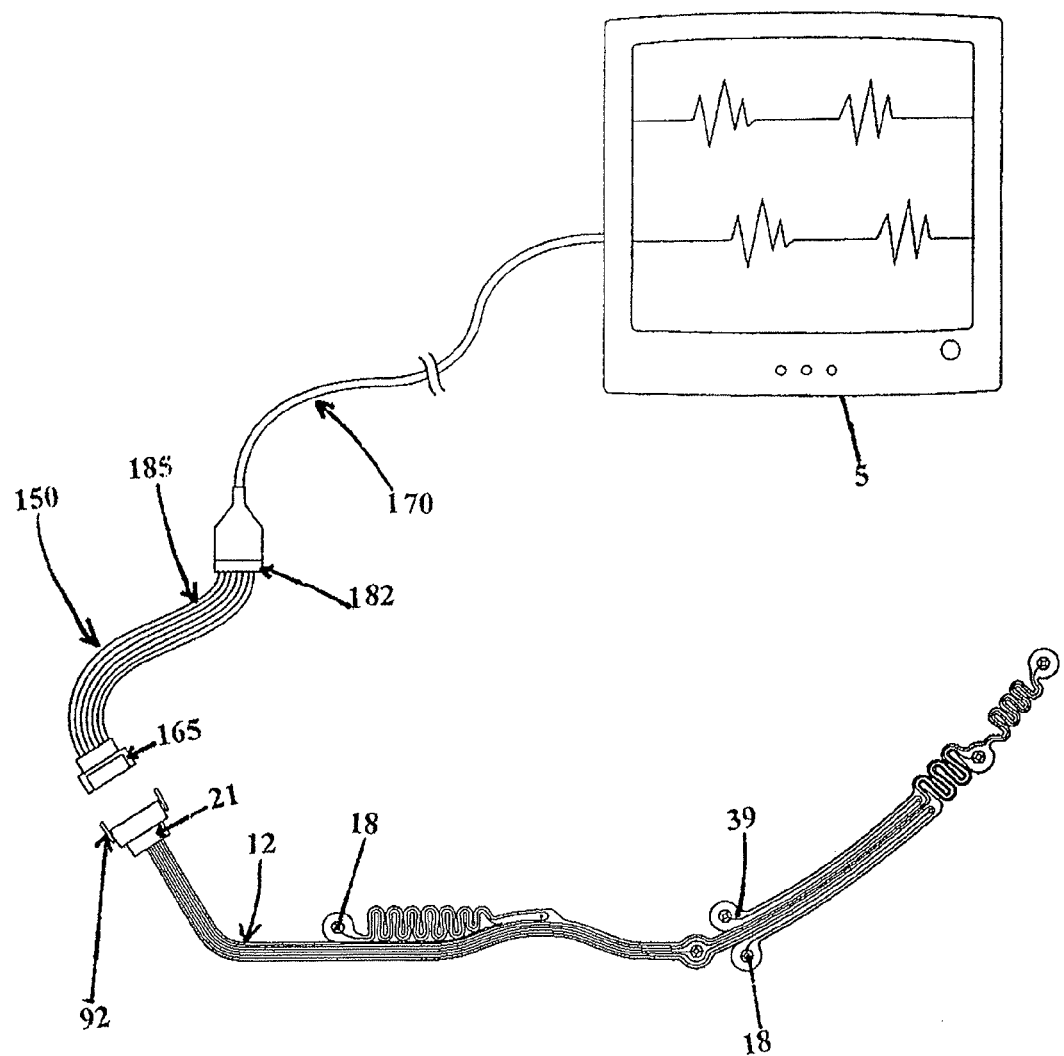
FIG. 10 is a perspective view of an exemplary embodiment of the adapter assembly as being used in an electrocardiograph system.

As shown in FIGS. 8, 9 and 10, the chest assembly connector 21 and the precordial assembly connector 66 may have retaining clips or flanges 92 located on the sides of the connectors 21, 66 for removably securing the connectors 21, 66 into the assembly ports by providing a bias or tension against the assembly ports. However, other means may be used to removably secure the connectors 21, 66 in the assembly ports, such as screws, pins or the like. The electrically conductive elements or traces 39 are specifically configured on the connectors 21, 66 so as to ensure that the electrical signals from the heart are properly transmitted to the body electronics unit 14. In other words, the electrically conductive elements or traces are sufficiently spaced apart or otherwise isolated in fixed positions in order to achieve the necessary creepage and clearance distances to prevent electrical arcing between the elements. In addition, the spacing between the electrically conductive elements or traces permits the chest assembly and the precordial assembly to withstand defibrillation shock. Furthermore, as shown in FIG. 1, the connectors 21, 66 may have ribs 96 for further electrical isolation between the conductive elements or traces and for preventing the electrically conductive elements or traces from coming into contact with metal objects or the like when the connectors 21, 66 are not inserted into the assembly ports.

Also shown in FIG. 1, the chest assembly connector 21 may have a sensor pin or ground pin 98 that completes a circuit within the body electronics unit 14 when the chest assembly connector 21 is plugged into the chest assembly port, thereby activating the power and bringing the body electronics unit 14 out of "sleep mode." The sensor pin 98 serves as a means for the body electronics unit 14 to identify the chest assembly 12 and to prevent the use of unauthorized chest assemblies or electrocardiograph wearables that are not designed to be used with the body electronics unit 14. In other words, the power of the body electronics unit 14 will not activate unless the body electronics unit 14 identifies or recognizes the sensor pin 98 of the chest assembly 12. For example, the sensor pin may have a specific tongue that corresponds and fits into a groove located in the chest assembly port.

As described above, the electrical signals are transmitted through the chest assembly and/or the precordial assembly to any conventional ECG monitor (including any legacy ECG monitor). In a preferred embodiment, the chest assembly and/or precordial assembly are connected to a body electronics unit 14, which is removably secured to the patient. For example, the body electronics unit 14 may be attached to the patient's arm using a releasable arm band. The body electronics 14 unit transmits the electrical signals to a base station (not shown) via radio transmission and may utilize two-way wireless communication protocols which are generally known in the art (e.g. BLUETOOTH® or WiFi®). The base station is a portable transceiver that can be placed in any location and does not necessarily have to be placed or secured in any fixed location. The base station is preferably removably secured to a stationary or portable ECG monitor via suitable mounting means. Alternatively, the base station can be incorporated into the monitor. There may be instances where a base station will not be in every ward or hospital room for use with the body electronics unit 14. In such instances, as shown in FIGS. 8-10, an adapter assembly 150 may be used to directly connect the chest assembly 12 or the precordial assembly 60 to the ECG monitor 5. In one exemplary embodiment, the adapter assembly 150 allows the chest assembly 12 or precordial assembly to be plugged directly into a conventional or existing telemetry transmitter. The adapter assembly 150 has an assembly receptacle 165 that connects to the chest assembly 12 or the precordial assembly 60 (not shown in FIG. 10) and a telemetry box receptacle 182 that connects to a conventional or existing telemetry transmitter (not shown in FIG. 10). In another exemplary embodiment, the adapter assembly 150 allows the chest assembly 12 or the precordial assembly 60 to be plugged directly into a conventional or existing ECG monitor trunk cable 170. Instead of having a telemetry box receptacle, the adapter assembly 150 has a cable assembly 185 for connecting to a conventional or existing ECG monitor trunk cable. In another exemplary embodiment, the adapter assembly 150 allows the chest assembly 12 or precordial assembly 60 to be plugged directly into standard lead wires that connect to an ECG monitor.

Figure 12:
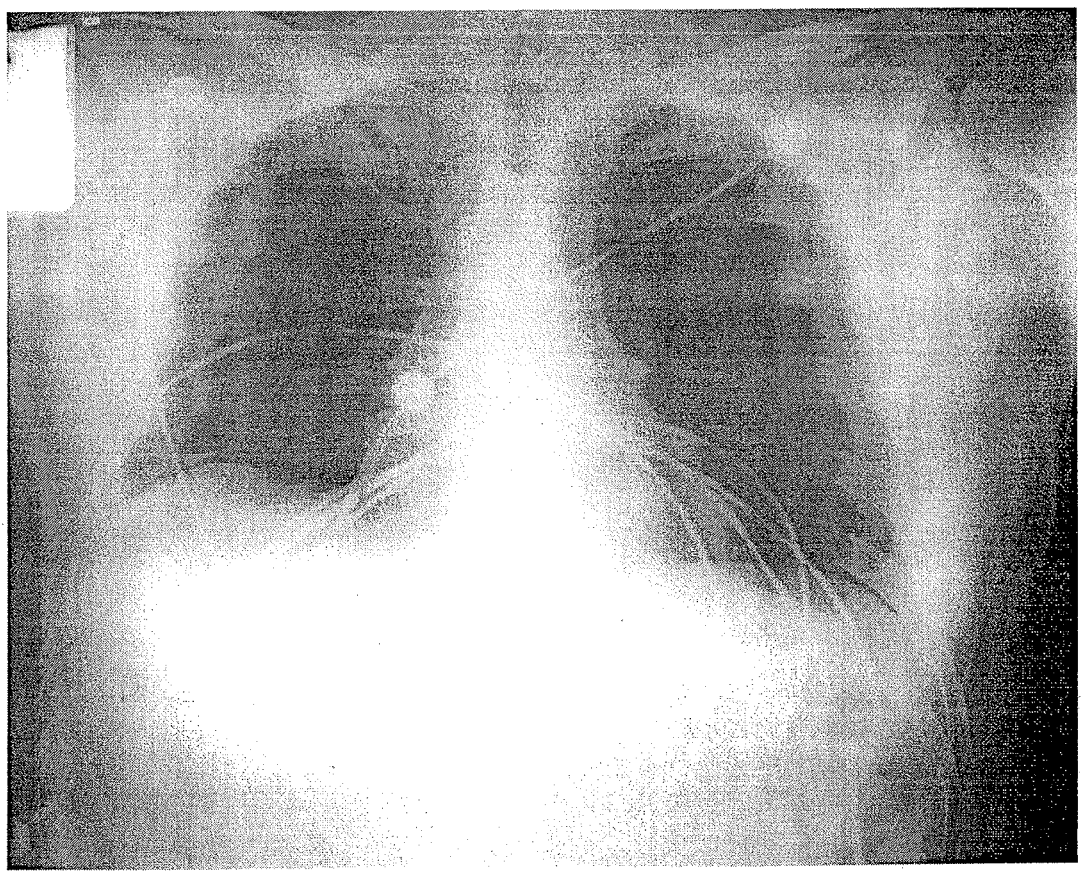
FIG. 12 depicts an x-ray film of a patient's chest in which standard lead wires were applied to the patient's chest.
Figure 12:
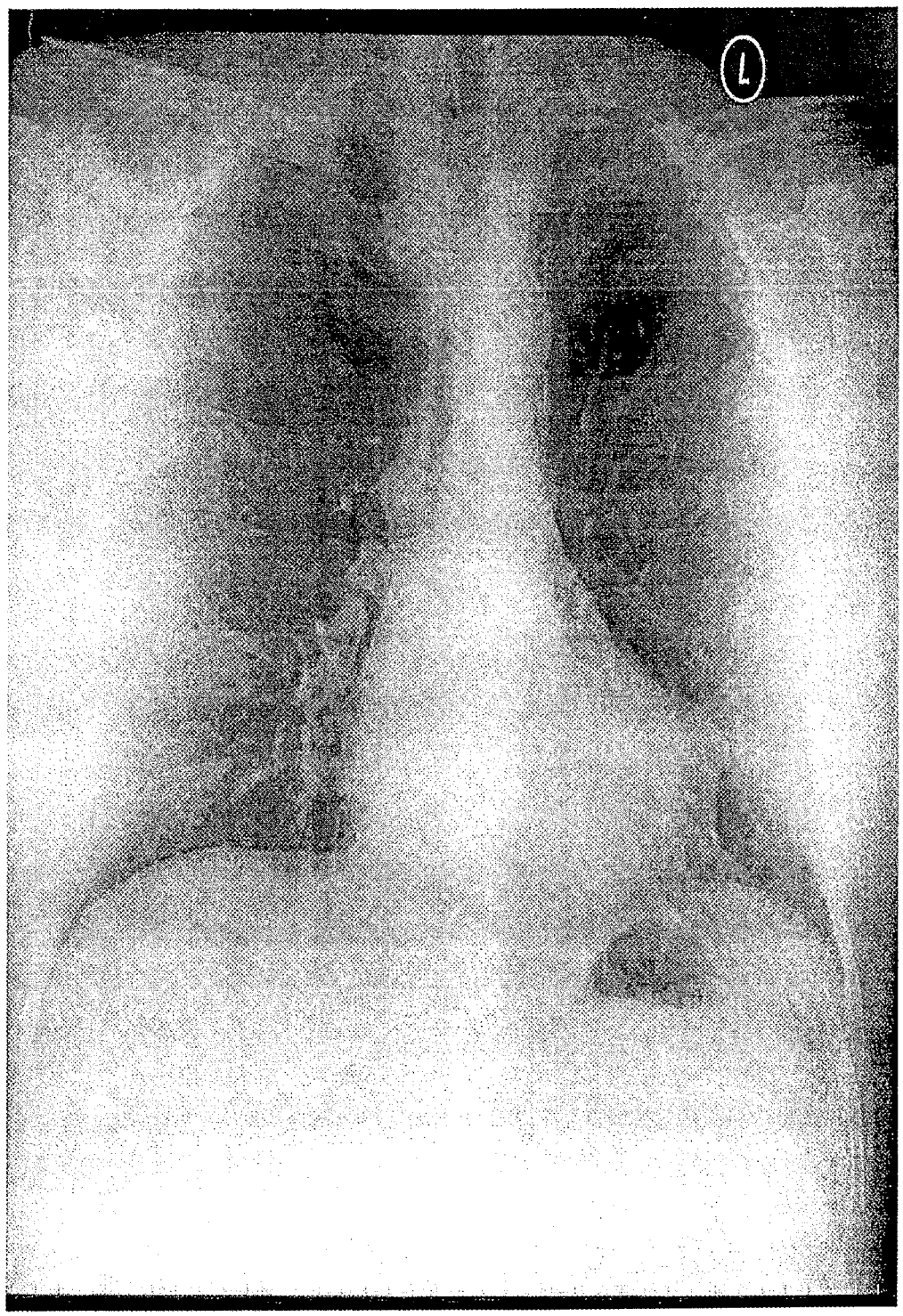

By way of example, one preferred embodiment of the electrode assembly is shown in FIG. 2, whereby the electrode assembly 12 was constructed of the following substantially radiolucent or radiotransparent layers: a skin-contacting outer layer 24 made of DuPont SONTARA® of 0.5 mm thickness, tri-laminate polyester adhesive layers 26 made of 4 Pillars Co. DSMI adhesive of 0.1 mm thickness, dielectric layers 30 and 32 made of Acheson Electrodag 452SS dielectric ink of 0.01 mm thickness, a conductive ink layer 39 made of Toyobo DW-351 silver ink whereby each conductive trace or element was 0.008 mm in thickness and 17 microns in width wherein each conductive trace or element was separated by a distance of 0.050 mm, an outer layer 22 made of Toray T60 polyester of 0.125 mm thickness, and an electrode housing 60 made of polyester and Poron of 5 mm thickness. The shape and configuration of the electrode assembly 12 was as depicted in FIG. 3. The conductive ink layer 39 at the electrode connector 18 terminated at the electrode connector 18 in the geometrical pattern shown in FIG. 6, whereby a substantial portion of the typical solid conductive area around the aperture 50 is clear except for two concentric circles 81 and 82 and 4 small axial connections 83 disposed between the two concentric circles. In an order to illustrate the improved radiolucency and radiotransparency of the electrode assembly and the electrode connector areas, non-metallic conventional electrodes (made by 3M) were affixed to an adult male chest and the electrode assembly, made of and constructed in the way just described, was connected to the electrodes and placed along the periphery of the chest in the positions shown in FIG. 8. An x-ray was taken thereafter and is shown in FIG. 12A. As indicated in FIG. 12A, the electrode assembly and the electrode connection points are substantially invisible and translucent in the x-ray thereby not obstructing or interfering with the appearance of the x-rayed subject and access to the chest and abdominal area. In contrast, FIG. 12 depicts an x-ray of an adult male chest whereby standard lead wires with snap electrode connections were applied to the chest. As you can see, the lead wires and the electrode connector portions are strongly visible on the x-ray and greatly interfere with the ability to view the x-rayed subject. Thus, the radiolucent and radiotransparent characteristics of the present invention are vastly improved over the standard lead wire equipment.

Although the various embodiments described above all concern electrocardiograph applications, the assembly of the present invention can be used to connect to a number of other sensors or electrodes for other monitoring applications without departing from the intended spirit or scope of the present invention. For example, sensors used to acquire pulse data, respiration rate data, EEG signal data or pulse oximeter data may all be used with the present invention.

In the foregoing description, the present invention has been described with reference to specific exemplary embodiments thereof. It will be apparent to those skilled in the art that a person understanding this invention may conceive of changes or other embodiments or variations, which utilize the principles of this invention without departing from the broader spirit and scope of the invention. The specification and drawings are, therefore, to be regarded in an illustrative rather than a restrictive sense. Accordingly, it is not intended that the invention be limited except as may be necessary in view of the appended claims.

We claim:

1. A method of positioning a substantially radiolucent electrode assembly on a patient that is being monitored for physiological signs such that access to the patient's chest is substantially unimpeded, comprising: applying the electrode assembly around the outer periphery of the patient's torso and proceeding around the back of the patient's neck, wherein the electrode assembly does not cross the patient's chest.

2. The method of positioning a substantially radiolucent electrode assembly on a patient that is being monitored for physiological signs such that access to the patient's chest is substantially unimpeded of claim 1 wherein the physiological sign is an ECG or EEG.

3. The method of positioning a substantially radiolucent electrode assembly on a patient that is being monitored for physiological signs such that access to the patient's chest is substantially unimpeded of claim 1 wherein the electrode assembly comprises a plurality of electrical connectors wherein each electrical connector is in electrical contact with a physiological sensor.

4. The method of positioning a substantially radiolucent electrode assembly on a patient that is being monitored for physiological signs such that access to the patient's chest is substantially unimpeded of claim 1 wherein a portion of the electrode assembly is routed around the back side of a patient.

5. The method of positioning a substantially radiolucent electrode assembly on a patient that is being monitored for physiological signs such that access to the patient's chest is substantially unimpeded of claim 4 wherein a portion of the electrode is routed around a patient's neck.

6. The method of positioning a substantially radiolucent electrode assembly on a patient that is being monitored for physiological signs such that access to the patient's chest is substantially unimpeded of claim 1 wherein said electrode assembly comprises:
  a flexible radiolucent non-conductive substrate having a proximal end and a distal end;
  at least one aperture formed in the substrate and sized to receive a sensor; and
  a conductive trace comprising a substantially radiolucent ink printed on the substrate for conducting a current between a sensor and the distal end of the substrate.

7. The method of positioning a substantially radiolucent electrode assembly on a patient that is being monitored for physiological signs such that access to the patient's chest is substantially unimpeded of claim 6 wherein the conductive trace comprises at least one linear conductor.

8. The method of positioning a substantially radiolucent electrode assembly on a patient that is being monitored for physiological signs such that access to the patient's chest is substantially unimpeded of claim 6 wherein the conductive trace comprises a plurality of substantially linear conductors.

9. The method of positioning a substantially radiolucent electrode assembly on a patient that is being monitored for physiological signs such that access to the patient's chest is substantially unimpeded of claim 6 wherein the conductive trace comprises a grid of linear conductors.

10. The method of positioning a substantially radiolucent electrode assembly on a patient that is being monitored for physiological signs such that access to the patient's chest is substantially unimpeded of claim 6 wherein the conductive trace comprises an encircling conductor which at least partially encircles the aperture.

11. The method of positioning a substantially radiolucent electrode assembly on a patient that is being monitored for physiological signs such that access to the patient's chest is substantially unimpeded of claim 10 wherein the conductive trace further includes a second inner conductive circle concentric with and in electrical contact to the encircling conductor.

12. The method of positioning a substantially radiolucent electrode assembly on a patient that is being monitored for physiological signs such that access to the patient's chest is substantially unimpeded of claim 11 wherein the inner conductive circle is divided by cuts in the substrate to form flaps wherein each divided portion of the conductive circle is in electrical contact with the encircling conductor.

13. The method of positioning a substantially radiolucent electrode assembly on a patient that is being monitored for physiological signs such that access to the patient's chest is substantially unimpeded of claim 11 wherein the inner conductive circle is a dot which is sized to minimally encircle the aperture while providing sufficient electrical contact with the sensor for the intended use.

14. The method of positioning a substantially radiolucent electrode assembly on a patient that is being monitored for physiological signs such that access to the patient's chest is substantially unimpeded of claim 6 wherein the conductive trace is sized to carry the current of a defibrillation shock.

15. The method of positioning a substantially radiolucent electrode assembly on a patient that is being monitored for physiological signs such that access to the patient's chest is substantially unimpeded of claim 14 wherein the conductive trace is around 17 microns wide.

16. The method of positioning a substantially radiolucent electrode assembly on a patient that is being monitored for physiological signs such that access to the patient's chest is substantially unimpeded of claim 6 wherein the conductive trace is comprised of copper, gold, carbon nanotube, indium tin oxide, silver, or graphite.

17. The method of positioning a substantially radiolucent electrode assembly on a patient that is being monitored for physiological signs such that access to the patient's chest is substantially unimpeded of claim 1 wherein said electrode assembly comprises:
  a flexible non-conductive substrate having a proximal end and a distal end;
  at least one aperture formed in the substrate and sized to receive a sensor;
  at least one conductive trace disposed on at least one surface of the non-conductive substrate wherein the conductive trace is capable of conducting a current between a sensor and the distal end of the substrate;
  at least one radiolucent electrical connector comprising at least one linear extension of the at least one conductive trace which extends to the aperture wherein the electrical connector is in electrical contact with the sensor; and an electrical cable between the distal end of the substrate and a monitor.

18. The method of positioning a substantially radiolucent-electrode assembly on a patient that is being monitored for physiological signs such that access to the patient's chest is substantially unimpeded of claim 17 wherein the at least one linear extension of the at least one conductive trace is comprised of a single dot of sufficient size to encircle the aperture.

19. The method of positioning a substantially radiolucent-electrode assembly on a patient that is being monitored for physiological signs such that access to the patient's chest is substantially unimpeded of claim 17 wherein the at least one linear extension of the at least one conductive trace is comprised of two concentric circles surrounding the aperture wherein the outer circle is connected to the inner circle by at least one coaxial trace.

20. The method of positioning a substantially radiolucent-electrode assembly on a patient that is being monitored for physiological signs such that access to the patient's chest is substantially unimpeded of claim 19 wherein the two concentric circles are partial circles.

21. The method of positioning a substantially radiolucent-electrode assembly on a patient that is being monitored for physiological signs such that access to the patient's chest is substantially unimpeded of claim 17 wherein the aperture forms at least one flap for engaging a sensor positioned through the aperture.

22. The method of positioning a substantially radiolucent-electrode assembly on a patient that is being monitored for physiological signs such that access to the patient's chest is substantially unimpeded of claim 17 further comprising a conductive adhesive located on at least one side of the electrode assembly.

23. The method of positioning a substantially radiolucent-electrode assembly on a patient that is being monitored for physiological signs such that access to the patient's chest is substantially unimpeded of claim 17 further comprising a plurality of electrode housings, each electrode housing positioned over an aperture formed in the electrode assembly and containing an elastomeric portion defining a female void for receiving a conductive portion of the sensor.

24. The method of positioning a substantially radiolucent-electrode assembly on a patient that is being monitored for physiological signs such that access to the patient's chest is substantially unimpeded of claim 17 further comprising an adapter that is configured to connect to the electrical connector such that the electrode assembly can be electrically connected to any conventional monitor.

25. The method of positioning a substantially radiolucent-electrode assembly on a patient that is being monitored for physiological signs such that access to the patient's chest is substantially unimpeded of claim 17 wherein the at least one electrical connector is movable to allow repositioning of the sensor around the outer periphery of the patient's torso such that access to the chest is substantially unimpeded.

26. The method of positioning a substantially radiolucent-electrode assembly on a patient that is being monitored for physiological signs such that access to the patient's chest is substantially unimpeded of claim 25 wherein a portion of the electrode assembly is intended to be positioned around the back of a patient's neck.

27. The method of positioning a substantially radiolucent-electrode assembly on a patient that is being monitored for physiological signs such that access to the patient's chest is substantially unimpeded of claim 17 wherein the electrical connector that connects to a conventional ground or a reference ECG electrode is in a fixed position on the perimeter of the torso to prevent the inadvertent placement of the electrode in an area that impedes access to the patient's chest.

28. The method of positioning a substantially radiolucent-electrode assembly on a patient that is being monitored for physiological signs such that access to the patient's chest is substantially unimpeded of claim 17 wherein the at least one electrical connector has sufficient current carrying capacity to withstand at least one defibrillation shock without being damaged.

29. The method of positioning a substantially radiolucent-electrode assembly on a patient that is being monitored for physiological signs such that access to the patient's chest is substantially unimpeded of claim 17 wherein the substrate is comprised of polyethylene terephthalate or a liquid crystal polymer.

30. The method of positioning a substantially radiolucent-electrode assembly on a patient that is being monitored for physiological signs such that access to the patient's chest is substantially unimpeded of claim 17 wherein the at least one conductive trace is comprised of copper, gold, carbon, carbon nanotube, indium tin oxide, silver, or graphite.

* * * * *